United States Patent
McKinley

(10) Patent No.: US 11,497,209 B2
(45) Date of Patent: Nov. 15, 2022

(54) COMPOSITIONS, METHODS, AND APPLICATIONS OF A SYNTHETIC SURFACTANT

(71) Applicant: Biome Solutions Inc., Victoria (CA)

(72) Inventor: Robert Scott McKinley, West Vancouver (CA)

(73) Assignee: 1283581 BC LTD, Victoria (CA)

( * ) Notice: Subject to any disclaimer, the term of this patent is extended or adjusted under 35 U.S.C. 154(b) by 155 days.

(21) Appl. No.: 16/915,900

(22) Filed: Jun. 29, 2020

(65) Prior Publication Data

US 2020/0404906 A1 Dec. 31, 2020

Related U.S. Application Data

(60) Provisional application No. 62/868,137, filed on Jun. 28, 2019, provisional application No. 63/000,141, filed on Mar. 26, 2020.

(51) Int. Cl.

| | |
|---|---|
| *A01N 25/30* | (2006.01) |
| *A01N 47/24* | (2006.01) |
| *A61K 31/05* | (2006.01) |
| *A61K 47/42* | (2017.01) |
| *A61K 9/127* | (2006.01) |
| *A01N 25/16* | (2006.01) |
| *C07K 14/46* | (2006.01) |

(52) U.S. Cl.
CPC ............. *A01N 25/30* (2013.01); *A01N 25/16* (2013.01); *A01N 47/24* (2013.01); *A61K 9/127* (2013.01); *A61K 31/05* (2013.01); *A61K 47/42* (2013.01); *C07K 14/463* (2013.01)

(58) Field of Classification Search
None
See application file for complete search history.

(56) References Cited

PUBLICATIONS

Rachel I. Fleming. Foam nest components of the Tungara frog: a cocktail of proteins conferring physical and biological resilience. Proceedings of the Royal Society of London B: Biological Sciences. Proc. R. Soc. B(2009)276, 1787-1795 (Year: 2009).*

* cited by examiner

*Primary Examiner* — Kagnew H Gebreyesus
(74) *Attorney, Agent, or Firm* — Richard Thomas Black; FisherBroyles LLP

(57) ABSTRACT

The present disclosure relates to a synthetic Túngara frog foam composition. The synthetic Túngara frog foam composition comprises six synthetically synthesized ranaspumin proteins (RSN-1 to RSN-6) wherein only the active segments of the RSN proteins are synthesized and six synthetically synthesized polysaccharides comprising four tetrasaccharides, a heptasaccharide and a nonasaccharide. Multiple novel applications of the foam are described.

9 Claims, 32 Drawing Sheets
Specification includes a Sequence Listing.

(A) Foam nest acquired from Dr. Gridi-Papp's research lab, (B) Tadpoles from foam nest after day 1, (C) Tadpoles after day 4, (D) Tadpoles going through metamorphoses, (E) Final growth stage of frogs Foam Polysaccharide analysis m/z 800-2000

Fragmentation pattern of the tetrasaccharide at m/z 967.49

Fragmentation pattern of the tetrasaccharide at m/z 981.50

Fragmentation pattern of m/z 1003.49

Fragmentation pattern of m/z 1017.51

Fragmentation pattern of m/z 1281.63

Fragmentation pattern of m/z 1744.84

Trypsin digest of proteins m/z range 50-500

Trypsin digest of proteins m/z range 50-500

Proposed Túngara frog foam nest glycoprotein structure (RSN-2, RSN-3, RSN-5 = surfactant proteins, RSN-1, RSN-4 and RSN-6 = binding proteins)

(Top) Floramite® (Bifenazate) (Bottom) 6 Pots Arabidopsis thaliana seedlings

Collected control and experimental leaves and the final homogenized leaf sample

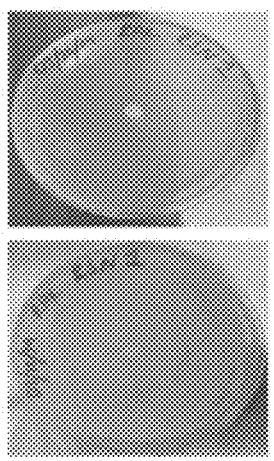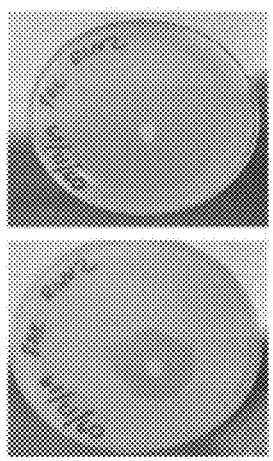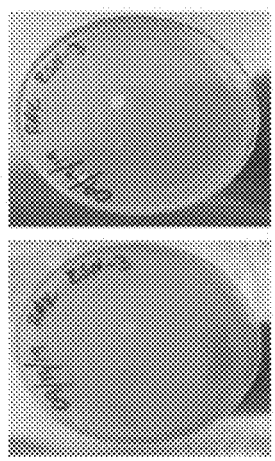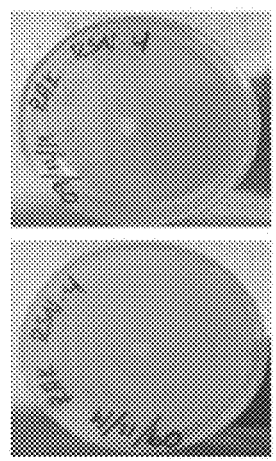
FIG. 23a                FIG. 23b

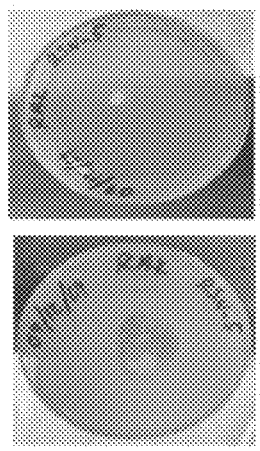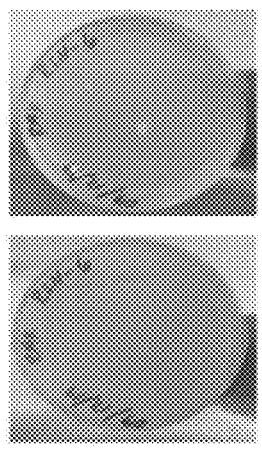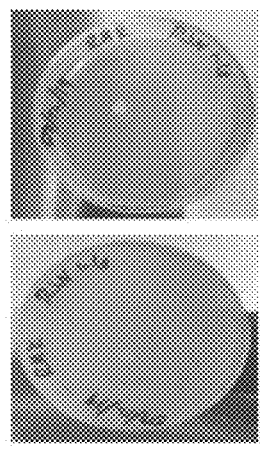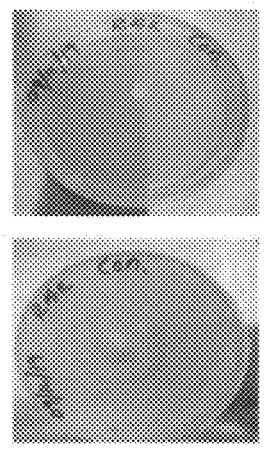
FIG. 24a     FIG. 24b
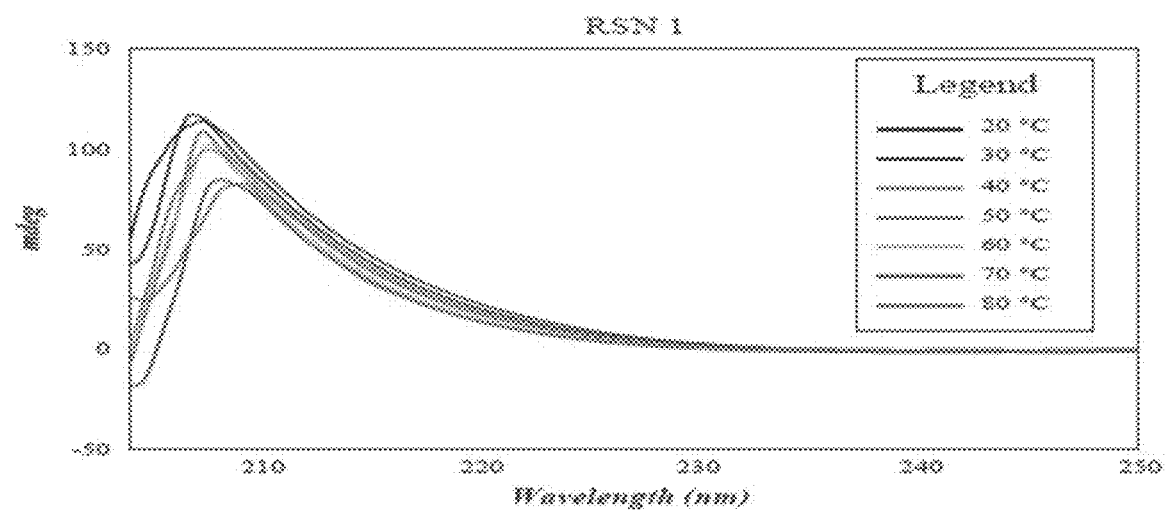
Denaturing of RSN 1 though a temperature ranging from 20 – 80°C
FIG. 25

Denaturing of RSN 2 though a temperature ranging from 20 – 90 °C

Denaturing of RSN 3 though a temperature ranging from 20 – 70 °C

Denaturing of RSN 4 though a temperature ranging from 20 – 90 °C

Denaturing of RSN 5 though a temperature ranging from 20 – 90 °C

Denaturing of RSN 4 though a temperature ranging from 20 –90°C

AFM image of liposomes without stabilizer after 24 hours. The black square is the location of the zoomed in image in Figure 31b.

Zoomed in AFM image of liposomes without stabilizer after 24 hours.

AFM image of liposomes with stabilizer after 24 hours. The black square is the location of the zoomed in image in Figure 32b.

Zoomed in AFM image of liposomes with stabilizer after 24 hours.

AFM image of liposomes without stabilizer after 96 hours. The black square is the location of the zoomed in image in Figure 33b.

Zoom in AFM image of liposomes without stabilizer after 96 hours.

AFM image of liposomes with stabilizer after 96 hours. The black square is the location of the zoomed in image in Figure 34b.

Zoom in AFM image of liposomes with stabilizer after 96 hours.

AFM image of liposomes with stabilizer after 96 hours.

AFM image of liposomes with stabilizer after 1 month. The black square is the location of the zoomed in image in Figure 36b.

Zoomed in AFM image of liposomes with stabilizer after 1 month. The black square is the location of the zoomed in image in Figure 36c.

Zoom in AFM image of liposomes with stabilizer after 1 month.

Microscope image of liposomes with stabilizer after 2 months.

SEQUENCE LISTING

```
<160> NUMBER OF SEQ ID NOS: 6

<210> SEQ ID NO 1
<211> LENGTH: 109
<212> TYPE: PRT
<213> ORGANISM: Engystomops pustulosus

<400> SEQUENCE: 1

Gly Gly Gly Asn Ile Gly Gly Gly Ala Lys Leu Gly Pro Glu Lys Pro
1               5                   10                  15

Ala Thr Pro Gly Ile Gln Asp Leu Leu Lys Ser Leu Leu Ser Val Leu
            20                  25                  30

Asn Leu Ser Pro Pro Ala Ile Pro Glu Asp Ala Glu Ala Val Ser Tyr
        35                  40                  45

Arg Asp Ala Lys Asn Gly Lys Phe Arg Leu Ile Lys Ile His Leu Gly
    50                  55                  60
```

```
Gly Glu Leu Tyr Cys His Val Lys Gln Ile Ala Gly Pro Ile Leu Ala
65                  70                  75                  80

Leu Pro Ile Val Ser Asp Val Val Glu Val Thr Gly Lys Glu Cys Gly
                85                  90                  95

Lys Thr Glu Asp Asp Pro Leu Glu Asp Phe Pro Ile Pro
            100                 105

<210> SEQ ID NO 2
<211> LENGTH: 96
<212> TYPE: PRT
<213> ORGANISM: Engystomops pustulosus

<400> SEQUENCE: 2

Leu Ile Leu Asp Gly Asp Leu Leu Lys Asp Lys Leu Lys Leu Pro Val
1               5                   10                  15

Ile Asp Asn Leu Phe Gly Lys Glu Leu Leu Asp Lys Phe Gln Asp Asp
            20                  25                  30

Val Lys Asp Lys Tyr Gly Val Asp Thr Lys Asp Leu Lys Ile Leu Lys
        35                  40                  45

Thr Ser Glu Asp Lys Arg Phe Tyr Tyr Val Ser Val Asp Ala Gly Asp
    50                  55                  60

Gly Glu Lys Cys Lys Phe Lys Ile Arg Lys Asp Val Asp Val Pro Lys
65                  70                  75                  80

Met Val Gly Arg Lys Cys Arg Lys Asp Asp Asp Asp Asp Asp Gly Tyr
                85                  90                  95

<210> SEQ ID NO 3
<211> LENGTH: 173
<212> TYPE: PRT
<213> ORGANISM: Engystomops pustulosus

<400> SEQUENCE: 3

Ile Asp Pro Thr Gly Leu Val Gln Ile Leu Leu Leu Glu Gln Val Val
1               5                   10                  15

His Lys Ile Pro Pro Gly Asn Ile Asn Leu Ala Arg Thr Gly Ile Ala
            20                  25                  30

Thr Gln Asp Ser Asp Tyr Thr Ala Ser Ala Val Pro Ser Glu Ala Arg
        35                  40                  45

Leu Ala Ile Asp Gly Asn Arg Asn Ser Asp Phe Asn Gln Lys Ser Cys
    50                  55                  60

Ser His Thr Gly Gly Asn Glu Pro Ala Trp Trp Arg Leu Glu Leu Lys
65                  70                  75                  80

Lys Lys Ser Lys Ile Ser Val Val Val Ile Ala Ile Arg Ser Asp Cys
                85                  90                  95

Cys Met Asp Arg Phe Lys Gly Ala Glu Leu Arg Ile Gly Asn Ser Gln
            100                 105                 110

Asp Ala Thr Val Asn Pro Ile Cys Gly Lys Val Ser Ala Val Lys Gly
        115                 120                 125

Ser Asn Tyr Leu Phe Cys Cys Asp Gly Met Glu Gly Lys Tyr Ile Ser
    130                 135                 140

Val Val Ile Pro Asp Arg His Glu Phe Leu Ser Leu Cys Glu Val Glu
145                 150                 155                 160

Val Tyr Gly Ala Lys Pro Ile Glu Gly Thr His Cys Lys
                165                 170

<210> SEQ ID NO 4
```

```
<211> LENGTH: 174
<212> TYPE: PRT
<213> ORGANISM: Engystomops pustulosus

<400> SEQUENCE: 4

Asp Arg Asn Leu Ala Leu Asp Gly Arg Ala Thr Met Ser Ser Ile Trp
1               5                   10                  15

Met Asp Pro Asp Ile Arg Gln Ser Phe Leu Gly Val Ala Met Asn Gly
            20                  25                  30

Ile Asp Gly Asn Thr Asp Ser Val Tyr Phe His Gly Ser Cys Phe His
        35                  40                  45

Thr Gly Leu Asp Ser Pro Ala Trp Tyr Arg Val Asp Leu Leu Arg Thr
50                  55                  60

Ser Lys Ile Ser Ser Ile Thr Ile Thr Asn Arg Gly Asp Phe Gly Ser
65                  70                  75                  80

Arg Thr Asn Gly Ala Glu Ile Arg Ile Gly Asp Ser Leu Ala Asn Asn
                85                  90                  95

Gly Asn Asn Asn Pro Arg Cys Ala Leu Val Thr Ser Ile Ala Asp Gly
            100                 105                 110

Glu Thr Arg Thr Phe Gln Cys Asn Asn Met Val Gly Arg Tyr Val Asn
        115                 120                 125

Ile Val Leu Thr Gly Lys Thr Glu Phe Leu His Leu Cys Glu Val Gln
130                 135                 140

Ile Phe Gly Glu Asn Leu Pro Arg Ser Phe Ser Cys Gln Tyr Ser Asn
145                 150                 155                 160

Asp Gly Met Ile Thr Leu Leu Val Ser Thr Arg Phe Met Lys
                165                 170

<210> SEQ ID NO 5
<211> LENGTH: 177
<212> TYPE: PRT
<213> ORGANISM: Engystomops pustulosus

<400> SEQUENCE: 5

Gly Ala Pro Gly Gly Ala Ala Gly Pro Leu Leu Val Leu Asn Ile Leu
1               5                   10                  15

Gly Ser Val Val His Glu Thr Lys Pro Pro Glu Gly Val Asn Leu Ala
            20                  25                  30

Leu Lys Gly Ile Ala Ser Ser Asp Ser Ile Ala Ser Asn Gly Ser Val
        35                  40                  45

Thr Gly Leu Ala Ala Lys Ala Ile Asp Gly Ile Arg Val Ser Asp Phe
50                  55                  60

Phe Lys Gly His Cys Ser Leu Thr Asn Gly Leu Asn Asn Pro Thr Trp
65                  70                  75                  80

Trp Lys Val Asp Leu Lys Lys Ser Tyr Lys Ile Ser Ser Val Phe Val
                85                  90                  95

Thr Asn Arg Asp Asp Cys Cys Thr Glu Arg Leu Leu His Ala Glu Ile
            100                 105                 110

Arg Ile Gly Ser Asn Pro Asp His Asn His Asn Pro Ile Cys Ala Glu
        115                 120                 125

Val Lys Thr Val Ala Ser Ser Asn Ile Gly Phe Cys Cys Gly Gly Met
130                 135                 140

Glu Gly Arg Tyr Val Ser Val Ser Val Pro Arg Lys Glu Gln Leu Ser
145                 150                 155                 160

Leu Cys Glu Val Glu Val Tyr Gly Asp Leu Lys Lys Val Leu His Cys
                165                 170                 175
```

Ala

<210> SEQ ID NO 6
<211> LENGTH: 230
<212> TYPE: PRT
<213> ORGANISM: Engystomops pustulosus

<400> SEQUENCE: 6

```
Glu Thr Leu Cys Ile Pro Gly Arg Met Lys Gln Leu Asp Ala Gly Ala
1               5                   10                  15

Gly Arg Val Val Ala Val Lys Ser Asn Gly Asp Val Tyr Gln Leu Leu
            20                  25                  30

Glu Asn Asn Trp Val Gln Ile Pro Gly Lys Leu Ile His Val Thr Val
        35                  40                  45

Gly Pro Ala Gly Leu Trp Gly Val Asn Lys Asp Lys Asn Ile Tyr Lys
    50                  55                  60

Tyr Val Asp Asn Asp Trp Leu Gln Val Asp Gly Leu Leu Asn Gln Ile
65                  70                  75                  80

Asp Ala Gly Gly Asn Arg Phe Val Val Gly Val Asn Asp Asn Glu Asp
                85                  90                  95

Ile Phe Cys Leu Asn Gln Asp Gln Thr Thr Ser Asn Ala Val Lys Leu
            100                 105                 110

Asp Tyr Lys Gly Val Asp Gly Lys Leu Lys Tyr Tyr Ser Ser Gly Gly
        115                 120                 125

Tyr Gly Ser Trp Gly Val Asn Ala Ala Tyr Asp Ile Phe Tyr Arg Arg
    130                 135                 140

Asn Val His Pro Met Ser Cys Gln Gly Thr Asn Trp Glu Asn Val Glu
145                 150                 155                 160

Gly Lys Leu Val Met Leu Glu Val Ala Glu Asp Gly Ser Val Tyr Gly
                165                 170                 175

Val Asn Tyr Asn Gly His Val Tyr Lys Arg Glu Gly Ile Thr Ala Gly
            180                 185                 190

Asn Pro Met Gly Thr Ser Trp Thr Tyr Leu Lys Val Asp Glu Lys Val
        195                 200                 205

Arg His Val Ser Tyr Asp Arg Gly Val Leu Tyr Val Val Thr Ile Asp
    210                 215                 220

Asp Arg Ile Phe Arg Cys
225                 230
```

COMPOSITIONS, METHODS, AND APPLICATIONS OF A SYNTHETIC SURFACTANT

PRIORITY CLAIM

This application claims priority from U.S. Provisional Application Nos. 62/868,137 filed Jun. 28, 2019 and 63/000,141 filed on Mar. 26, 2020. The above-referenced applications are hereby incorporated by reference in their entireties as if fully set forth herein.

STATEMENT REGARDING SEQUENCE LISTING

The Sequence Listing associated with this application is provided in text format in lieu of a paper copy, and is hereby incorporated by reference into the specification. The name of the text file containing the Sequence Listing is Sequence_Listing_222857_1.txt The text file is 9 KB, was created on Jun. 29, 2020, and is being submitted electronically via EFS-Web.

TECHNICAL FIELD

The present disclosure relates generally to material science and more specifically, to biochemistry and molecular biology. The subject matter of the present disclosure concerns the synthetic synthesis of Túngara frog foam including its proteins and polysaccharides for use in various applications.

BACKGROUND

The production of foams from animals is not an uncommon reproductive trait in many organisms[1]. However, some organisms produce a surfactant foam that is stable for many days.

These foams can stable for up to 57 days and are resilient to weather changes in the environment.[2-3] These foams tend to be aqueous foams using protein based surfactants. One specific organism, *Engystomops pustulosus*, more commonly known as the Túngara frog, has been largely studied over the use of its reproductive foam[4]. This species has an interesting foam structure because the foam contains an anti-fungal and an anti-microbial attribute that is not common among other species[5]. Furthermore, the anti-microbial and anti-fungal attributes does not disrupt or cause apoptosis of the embryos of the frogs.

The foam can be stable for up to 10 days without any dehydration or loss of foam structure due to surface tension effects[1]. Interestingly the foam is comprised only of proteins and polysaccharides[6]. No known detergents or surfactants have been identified in this foam in previous literature. As a result of this interesting lack of detergents the proteins have been largely studied for their use as a surfactant[7-8]. The Túngara frog foam nest has 6 unique proteins that have been deemed the ranaspumin proteins. These proteins go from ranaspumin (RSN) 1 to RSN 6, with RSN 2 being the main protein in the frog foam that acts as the surfactant. These proteins have been found to be fucolectin type proteins that bind to the hydroxyl group at the 1 position of the polysaccharide[9]. These surfactants are what stabilize the foam nest[1]. The proteins of the foam have already been previously studied and synthesized using recombinant DNA techniques[1]. The sequences of the proteins have been characterized using PCR analysis, however no study has developed a method to characterize the polysaccharides of the foam. Without the polysaccharides, the foam is only 10 angstroms thick, while the foam collected from a Túngara frog foam nest is 85 angstroms thick. Without the polysaccharides, the foam cannot be artificially synthesized.

One study attempted to determine the saccharides in the frog foam nest by reacting the proteins with different monosaccharides to determine their solubility. This study proved that the proteins rsn1-6 were only soluble with galactose, which is common of fucolectin type proteins. The characterization of polysaccharides is challenging in that polysaccharides do not easily accept a charge for mass spectrometry[10]. The use of matrix assisted laser desorption ionization (MALDI) coupled to mass spectrometry (MS) only recently allowed for the characterization of polysaccharides[11]. This research project used MALDI-MS coupled to determine the structure and sequence of the polysaccharides in the Túngara frog foam to allow for the artificial synthesis of the frog foam nest. In total 6 polysaccharides were found in the frog foam nest and all 6 of the polysaccharides have been sequenced to determine each individual monosaccharide that comprises the polysaccharide.

SUMMARY

The present disclosure includes a combination of biochemical/molecular biology methodology to characterize a unique synthetic organic surfactant protein that lends itself to a diverse number of applications.

The Túngara frog foam nest has 6 unique proteins that have been deemed the ranaspumin-1 (RSN-1) through ranaspumin-6 (RSN-6) proteins. The production of foam from the Túngara frog has been largely studied for its surfactant capabilities as these proteins can create a natural foam. This natural foam nest can be stable for up to 10 days without any dehydration or loss of foam structure due to surface tension effects. Interestingly, no research group has been able to mimic this stability in the artificial synthesis of this foam.

The present disclosure may include novel synthesis of only the active segment of the RSN proteins, which results in proper folding of the protein, allowing the desired surfactant capabilities to be retained in a synthetic foam. An embodiment describes successfully synthesized RSN 1 through 6 using only the active amino acid chain, as well as a number of novel applications for the resulting surfactant foam.

In accordance with some examples of the present disclosure, a novel synthetic surfactant protein foam is described with improved stability and longevity.

In accordance with other examples of the present disclosure, the synthetic surfactant protein foam is used to significantly enhance the efficacy of fracking and sustainable separation of oil in tar sands deposits.

In accordance with still further examples of the present disclosure, the synthetic surfactant protein foam is used to greatly increase the growth and production of cultured plants.

In accordance with yet other examples of the present disclosure the synthetic surfactant protein foam is used to enhance viability and transportation of live organs.

In accordance with still another example of the present disclosure, the synthetic surfactant protein foam is used to improve the transportation and longevity of seafood.

These and other examples of the present disclosure are described in further detail below.

BRIEF DESCRIPTION OF THE DRAWINGS

FIGS. 23a and 23b shows a Kirby Bauer antimicrobial assay of RSN 1-4, shown at 0 hours and after 24 hours of incubation.

FIGS. 24a and 24b shows a Kirby Bauer antimicrobial assay of RSN 5-6, RSN 1-6 mixture and control sample, shown at 0 hours and after 24 hours of incubation.

FIG. 25 shows a spectra analysis of denaturing of RSN 1 through a temperature ranging from 20° to 80° C.

DETAILED DESCRIPTION

Throughout the following description, specific details are set forth in order to provide a more thorough understanding of the present teaching. However, the subject matter of the present teaching may be practiced without these particulars. In other instances, well known elements have not been shown or described in detail to avoid unnecessarily obscuring the present teaching. Accordingly, the specification and figures are to be regarded in an illustrative, rather than a restrictive, sense.

The synthetic RSN proteins described herein can be modified by reducing the number of amino acids in the synthesized protein to only include the DNA code for the mature RSN proteins. RSN proteins are synthesized in a precursor form, having an amino-terminal hydrophobic signal peptide.

Figure 1:
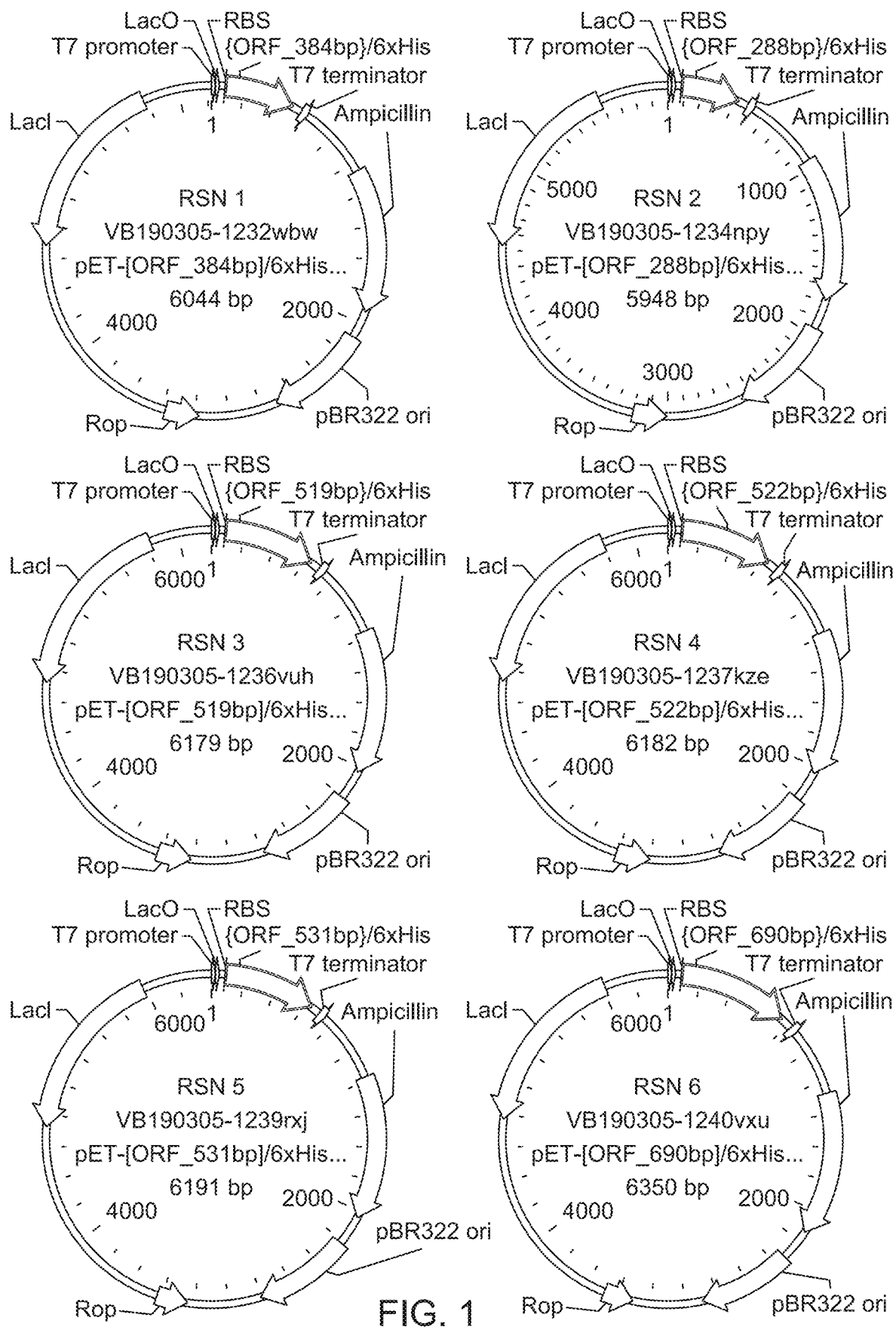
FIG. 1 shows exemplary vectors which may be used for RSN proteins. The vectors shown are designed vectors for each ranaspumin protein synthesized.

In Eukaryotic cells, this signal peptide directs proteins to the secretory apparatus, by association with and insertion into the endoplasmic reticulum (ER). During this process, the signal peptide is proteolytically cleaved by membrane bound enzymes that specifically perform this function. The active form is known as the mature peptide and in some instances is unable to function until this signal peptide is removed. In this method, the active RSN proteins were recombinantly synthesized in bacteria using the mature amino acid sequence. This mature sequence was shown to have an increased activity compared to the precursor form, as demonstrated by the longevity and stability of the foam produced.

The genetic sequences for each of the 6 RSN proteins according to the present disclosure are as follows:

```
RSN-1 (384 bp)
(Syntetic Amino Acid Sequence No. 1)
GGGNIGGGAKLGPEKPATPGIQDLLKSLLSVLNLSPPAIPEDAEAVSYRD

AKNGKFRLIKIHLGGELYCHVKQIAGPILALPIVSDVVEVTGKECGKTED

DPLEDFPIP

RSN-2 (288 bp)
(Synthetic Amino Acid Sequence No. 2)
LILDGDLLKDKLKLPVIDNLFGKELLDKFQDDVKDKYGVDTKDLKILKTS

EDKRFYYVSVDAGDGEKCKFKIRKDVDVPKMVGRKCRKDDDDDDGY

RSN-3 (519 bp)
(Synthetic Amino Acid Sequence No. 3)
IDPTGLVQILLLEQVVHKIPPGNINLARTGIATQDSDYTASAVPSEARLA

IDGNRNSDFNQKSCSHTGGNEPAWWRLELKKKSKISVVVIAIRSDCCMDR

FKGAELRIGNSQDATVNPICGKVSAVKGSNYLFCCDGMEGKYISVVIPDR

HEFLSLCEVEVYGAKPIEGTHCK

RSN-4 (522 bp)
(Synthetic Amino Acid Sequence No. 4)
NRNLALDGRATMSSIWMDPDIRQSFLGVAMNGIDGNTDSVYFHGSCFHTG

LDSPAWYRVDLLRTSKISSITITNRGDFGSRTNGAEIRIGDSLANNGNNN

PRCALVTSIADGETRTFQCNNMVGRYVNIVLTGKTEFLHLCEVQIFGENL

PRSFSCQYSNDGMITLLVSTRFMK

RSN-5 (531 bp)
(Synthetic Amino Acid Sequence No. 5)
GAPGGAAGPLLVLNILGSVVHETKPPEGVNLALKGIASSDSIASNGSVTG

LAAKAIDGIRVSDFFKGHCSLTNGLNNPTWWKVDLKKSYKISSVFVTNRD

DCCTERLLHAEIRIGSNPDHNHNP;ICAEVKTKASSNIGFCCGGMEGRYV

SVSVPRKEQLSLCEVEVYGDLKKVLHCA

RSN-6 (690 bp)
(Synthetic Amino Acid Sequence No. 6)
ETLCIPGRMKQLDAGAGRVVAVKSNGDVYQLLENNWVQIPGKLIHVTVGP

AGLWGVNKDKNIYKYVDNDWLQVDGLLNQIDAGGNRFVVGVNDNEDIFCL

NQDQTTSNAVKLDYKGVDGKLKYYSSGGYGSWGVNAAYDIFYRRNVHPMS

CQGTNWENVEGKLVMLEVAEDGSVYGVNYNGHVYKREGITAGNPMGTSWT

YLKVDEKVRHVSYDRGVLYVVTIDDRIFRC
```

The molecular weights of the RSN proteins are 11.38 kDa, 11.11 kDa, 18.85 kDa, 19.26 kDa, 18.73 kDa, and 25.69 kDa for RSN-1, RSN-2, RSN-3, RSN-4 RSN-5, and RSN-6, respectively with no histidine tags attached.

This protein sequence may be modified such that the synthetic example produces only the mature RSN proteins. Both eukaryotic (higher order organisms) and prokaryotic (bacterial) cells use signal peptides to direct proteins to their respective secretory mechanism. In fact, many signal peptides derived from eukaryotic hosts are known to be efficiently removed when expressed in prokaryotic hosts.

Protein production can be performed with accumulation designed to take place outside as well as inside bacterial cells: External protein purification strategies rely on the cellular secretory mechanism for the production and accumulation of protein products outside of the cell in the medium. In these cases, proteins can have an amino-terminal signal peptide in order to take advantage of the secretory apparatus, which is cleaved by membrane-bound proteases. Purification follows, since the mature protein appears as a relatively pure product in the supernatant after the cells have been pelleted away by centrifugation. This method may not always be possible, since some proteins may not be stable in the extracellular milieu, and its purification requires concentrating very large volumes of medium. In addition, strong induction of protein production may overrun the secretory apparatus, resulting in the accumulation of the precursor product inside the cell in the form of inclusion bodies. One possible approach, as described herein, is to avoid the secretory apparatus altogether, synthesizing the mature form directly. This embodiment led to high production of the mature active form with no contamination by the precursor foam. Thus this approach provides a higher yield of the synthetic mature protein that can properly fold and that retains the characteristics of the active product. Although we have used the internal accumulation approach, it is expected that had we used the approach that used the secretory pathway, leading to external accumulation of the mature product, we would have gotten equivalent results.

Description of Exemplary Production Method

Various techniques that are well known in the art and may be employed to produce one or more of the synthetic RSN proteins described above. The following description details one embodiment of a non-limiting process used to achieve satisfactory results. Of course, one of ordinary skill in the art understands that not all of the individual steps and details of the purification process are necessary for attaining the results we have observed, and many alternatives are contemplated and possible. The production phases of the present disclosure include: *DNA Vector Design, Bacterial Growth, Protein Expression, Protein Purification, Foam Stability*, and *Mass Spectra Characterization*. The phases have all resulted in the synthesis of artificial RSN proteins that maintain surfactant capabilities. These phases are described in detail below. Again, the steps are simply one example of a method of synthesizing the RSN foam, and are not meant to be limiting.

DNA Vector Design

In preparing the subcloned RSN genes that are inserted into the DNA Vector, DNA corresponding to between 1-23 amino acids were eliminated from the gene sequence. According to various embodiments of the present disclosure, a vector for each of the 6 RSN proteins is designed to contain an ampicillin resistance gene allowing only transformed (vector containing) cells to grow. Furthermore, the presently described vector design contains a LacO gene promoter upstream of the subcloned RSN gene, which ensures that the RSN protein is only expressed upon induction with isopropyl β-D-1-thiogalactopyranoside (IPTG). This vector is also compatible with the host, which, in this exemplary embodiment, was BL21 (DE3) bacteria. (See FIG. 1).

Bacterial Growth

According to the presently described embodiment of the disclosure, transformed cells containing each vector were delivered from the manufacturer (VectorBuilder) as a 50:50 glycerol:water stock solution. These were stored −80° C. in order to prevent cell death. Upon removal from the freezer, the bacterial strains were streaked onto Lysogeny Broth (LB) ampicillin agar plates to allow the E. coli to grow and incubated overnight at 37° C. These streaks developed into individual colonies. Once the colonies were of sufficient size, they were inoculated into small LB ampicillin 100 mL cultures. In alternative embodiments, the first inoculation from plates may be made into a 1-2 ml culture, after which, they may be transferred the next day into a 100 ml culture. These cultures were grown for 2 days at 37° C. with continuous shaking until the optical density was 0.6. Next, 1 L of LB ampicillin media was inoculated with 20 mL of solution from the small 100 mL cultures and placed in an incubator shaker at 37° C. for 6 hours.

Isolation of Plasmid

In order to verify that the bacterial cells from VectorBuilder, have the correct insert, the inventor includes a description of the process used to purify the vector. This process has many commercial embodiments available. A person of ordinary skill in the art will readily understand the available methods that may be used to complete this step. According to an embodiment of the present disclosure, the plasmid was isolated. Single colonies of E. coli cells containing plasmids with sequences for RSN1-6 were obtained by streak plating the glycerol stock on LB ampicillin plates. One individual colony was picked up from each plate (RSN 1-6) and inoculated in 5 ml of liquid LB media (with Ampicillin) in glass test tubes, and grown overnight at 37° C. with shaking for isolation of the plasmid the next day. The Optical Density (O.D.) of the cultures were checked the following morning prior to the plasmid isolation, and were estimated to be around 0.8-1. In this particular embodiment, the alkaline lysis method standardized by Birnboim and Doly (1979) was followed to isolate the plasmid DNA from the bacterial cultures. The collected aliquots were transferred to 1.5-ml Eppendorf tubes and spun them down twice at 13000 rpm for 1 min on a table-top centrifuge. The supernatant was discarded and the liquid was removed completely by turning the tube upside down onto a piece of Kim wipe for a few seconds. Next, 100 μl of resuspension solution (P1 buffer) was added into each tube, and vortexed to completely resuspend cell pellets, followed by 100 μl of lysis solution (P2 buffer) and mixed by gently inverting the tube 5-6 times. The solutions quickly turned transparent and became more viscous, indicating bacterial lysis had taken place. Then 150 μl of neutralizing solution were added (P3 buffer) and mixed by inverting the tubes several times. At this point bacterial chromosomal DNA is usually seen as a white precipitate. The test tubes were centrifuged at 13000 revolutions per minute (rpm) for 10 min and then the supernatants were carefully transferred, without disturbing the white precipitate, to new labeled 1.5-ml Eppendorf tubes. 2 mL of absolute cold ethanol were added to each tube and mixed by inverting the tubes a few times. They were spun down to precipitate plasmid DNA (transparent pellets) at 13000 rpm for 10 min. Then, the supernatants were discarded followed by the removal of the remaining liquid by leaving the tubes upside-down on pieces of Kim wipes; they were later left to air dry for 10-20 min. Finally, the plasmid DNA pellets were dissolved with 50 μl Tris-EDTA buffer by pipetting solutions several times to promote mixing of the pellet. The extracted plasmids, were run on a 1% Agarose gel with 1× TAE buffer and stained with ethidium bromide (EtBr) for visualization in a UV gel doc imaging system.

In alternative examples of the present disclosure, in order to confirm that individual cultures contained the DNA vectors of the correct size, aliquots can be taken from the growing cultures and DNA vector purification can be performed. It should be understood that there are many well know and commercially available methods for purifying vector constructs from bacterial cells, these are called minipreps or maxi-preps by those familiar with the art.

PCR Amplification of RSN1-6 Insert Using Sequence Specific Primer

According to the described embodiment of the present disclosure, the vector is much larger than the inserted DNA sequence, therefore it is optionally advantageous to further confirm that the inserted gene sequence is of the correct size. There are several methods one may choose to do this and these are familiar to one practiced in this art. For instance, one may use restriction enzymes to remove specific segments of the gene and confirm their size. One may also perform sequencing of the inserted region. According to one embodiment, PCR and gel electrophoresis is used, and 22 μl of nuclease free distilled water to set the total volume of the mixture at 50 μl. A standard 35-cycle PCR reaction was run using a Flexlid Thermal Cycler (Eppendorf, N.Y., USA). The 15 μl of amplified PCR product was ran on a 1% Agarose gel using 1×TAE buffer and stained with ethidium bromide (EtBr) for visualization of products. For validation of the product PCR size, 10 μl of 100 bp ladder (NEB, MA, USA) was used. Using the sequence specific primers, RSN-1 was supposed to give a 386 bp product, RSN-2 (290 bp product), RSN-3 (521 bp product), RSN-4 (524 bp product), RSN-5(533 bp product) and RSN-6 (692 bp product). Successful cloning of insert sequences in the recombinant vectors was found. The PCR bands were shown to match the expected size when compared with the 100 bp ladder size. This result validates that the recombinant E. coli cells have the RSN1-6 sequences inside the plasmids which have been transformed into them.

Protein Expression

Once the bacterial cells were grown, and with confirmation that the growing bacterial cultures have the correct insert, the RSN proteins may be expressed by placing Isopropyl β-D-1-thiogalactopyranoside (IPTG) into the culture to a final concentration of 1 mM and left overnight at room temperature with shaking. Once expression of the proteins is complete, the large culture is removed and purification of the proteins begins.

Protein Purification

Many purification techniques are available in the art. Persons of ordinary skill in the art understand that various alternatives are available and that the following detailed disclosure is simply one non-limiting embodiment of a purification technique that may be used. Further, different purification techniques may be used or may vary from one RSN to another. Protein purification can be carried out using an adaptation of the Nickel-Affinity Chromatography Process. Cell pellets from 1 L culture were centrifuged for 20 minutes at 10,000 rpm. Alternative speeds are of course known to those in the art as a means of separation. The supernatant is removed and discarded. The remaining pellets are then combined and frozen at −80° C. The pellets are removed and 40 mL of NPI-10 buffer is added to each of the tubes. The tubes are then subjected to sonication using a cell dismembrator. The tubes are placed in an ice bath and sonicated at 30 seconds on and 1 minute off intervals at 80% amplitude. After sonication, the samples were placed in the centrifuge at 4° C. and run at 12,000 rpm for 20 minutes. This run was conducted a second time to ensure no cell fragments remained in the supernatant. The supernatant is then removed and stored at 4° C. overnight.

The samples may then be subjected to nickel affinity column purification to extract only the proteins of interest using a Novagen His-Bind Resin Purification Kit. This kit allows up to 10 mg of each protein to be extracted during each run. The process begins by placing 2 mL of resin into the column and letting the resin settle using gravity filtration. Next, 5 mL of charge buffer are placed in the column to provide the nickel substrate of the column, which the protein can bind to due to the histidine tag on the protein. Once the charge buffer is completed, 3 mL of binding buffer are used to clean the column of any contaminants. The sample extract (200 mL) is then placed on the column. To ensure proper extraction, a flow of 10 mL per hour is used. Once the sample extract is completed, another wash is performed to remove all contaminants in the column. Finally, an elution buffer is used to extract the protein from the column into 6 mL of buffer. This buffer is then removed and upon agitation a foam is formed.

A secondary purification is performed. A secondary purification, according to this exemplary embodiment, is used to concentrate the protein solution from 1 mg/mL to 10 mg/mL, using a Sartorius Vivaspin 20 centrifugal tube. In this embodiment, for example, the tube has a 10,000 molecular weight cut off (MWCO), allowing only proteins larger than 10,000 molecular weight to remain in the solution. This solution is then extracted and lyophilized overnight to remove all remaining contaminants and solvents from the proteins. The proteins are then analyzed using Electrospray Ionization coupled to Mass Spectrometry (ESI-MS) and Matrix Assisted Laser Desorption Ionization coupled to Mass Spectrometry (MALDI-MS) for confirmation of protein synthesis. In alternative arrangements, SDS-PAGE gels may also be used for size verification.

In further alternative embodiments, for the purification of proteins from inclusion bodies, the use of mild denaturing agents like Urea and or GdnHCL applied at low concentrations can be used to improve the yield from cellular inclusion bodies.

Foam Stability

The method reported here, as well as other methods and alternatives known in the art, allow for substantially increased foam stability across all 6 RSN proteins. The described method, for example, produces foam having a stability that far surpasses previously reported synthesis methods.

The described method teaches recombinant synthesis of active RSN proteins using a shortened amino acid sequence. Due to the lack of additional amino acids in the protein, the method according to the present disclosure achieved substantially increased foam stability than suggested in the prior art. In certain cases, foam stability may be greater than 10 days and may possess stability that is at least 5 times or more than that of natural ranaspumin proteins without any dehydration or loss of foam structure due to surface tension effects. The reduced number of amino acids in the synthesized proteins also allows for proper folding of the synthetic protein as the possibility of misfolding is significantly reduced. In short, when there are more amino acids in the synthesized proteins, misfolding is more likely to occur which limits the capabilities of the synthetic foam to mimic the natural ranaspumin structure.

In alternative embodiments, other methods for synthesizing proteins are used, including chemical synthesis using stepwise elongation, fragment condensation, and even chemical ligation.

Novel Applications of Surfactant Protein

The surfactant protein foam can be applied to various scenarios in order to achieve results not previously available with prior art techniques. The surfactant protein complex displays water favoring (hydrophilic) and water adverse tails (hydrophobic), allowing it to bridge interfaces between aqueous and membranous environments. Applications for such molecular complexes are extremely diverse and vary from life preserving environments, stabilizing drug delivery systems, improving oil extraction methods, to ensuring the continued growth in the food production sector.

The hydrophobic and hydrophilic tails of the protein and associated polysaccharide moieties act in concert to give this protein complex its specific activity. The unique structure and properties of this protein complex are responsible for the diverse applications of this protein in a variety of commercial sectors. For example, the sugar back bone of the present disclosure ensures the long-lived integrity of the protein, which improves its usefulness. Large quantities of the protein can be readily produced using recombinant technology, thereby eliminating any issue related to scalability for the protein product.

Drug Delivery

Surfactants that are used in pulmonary drug delivery include polysorbate 80, poloxamer 407, and surfactin. These prior art surfactants can be replaced with the novel surfactant proteins of the present disclosure. This technique eliminates the necessity of using toxic surfactants for pulmonary drug delivery while still maintaining enhanced absorption of the drug.

Oil and Gas Industry Application

One inventive application of the surfactant foam as described in the present disclosure is the application of the foam in the oil and gas industry to improve yields and lower costs. A main problem in the oil and gas industry is the use of toxic chemicals during the fracking process. With the aid of these novel organic surfactants, fewer toxic chemicals will be used, which can lead to a "green" fracking process.

More specifically, according to an embodiment of the present disclosure, the described surfactant foam may be used in and benefit the fracking process. Fracking is the process of extracting gases and liquid hydrocarbons from underground deposits, by drilling (mainly by converting vertical to horizontal). In the zones which contain the desired gas/liquid, the drilling tube is perforated and the deposit rock is "fractured" by injecting liquid under high pressure (of the order of tens of thousands psig). The temperature used depends on the depth of the rock and can be of 200-300° F. The liquid used for fracking contains added surfactants, salts, sand, etc. In fracking, it is ideal to retrieve all fracking materials, that way they and are not allowed to remain in the ground where they may contaminate the ground water. Application of the surfactant foam assists in the flow of material reducing friction during the fracking of sediment. The foam assists in the release of oil and gas. For example, the surfactant protein can aid in the release of oil and gas as the protein is capable of binding to the oil and gas while still being dissolved in an aqueous solution. Once the aqueous solution is made consisting of oil and gas, protein, and solvent, the solution can be filtered using a tangential flow filtration system to release the oil and gas from the protein.

Tar sands, or oil sands, also present an opportunity and embodiment of the present disclosure. Tar sands are a mixture of sand and bitumen. Natural bitumen is a paste-like material made of organic material, mainly hydrocarbons, but containing also oxygen and other atoms. The separation of sand and bitumen is performed by warming the mass of sand-bitumen by steam, with or without addition of some petroleum diluent. The separation of the 3 phases (sand, bitumen and water) can be helped by use of surfactants (detergents), such as the surfactant foam described in the present disclosure. The processing of the produced waste (sand and water) is a major problem. In an embodiment of the present disclosure, organic surfactant of the present disclosure is applied and naturally can separate any oil from all substrates, including the sand. This organic surfactant binds the oil from the tar sands and the sand can be filtered out of the solution, leaving only the surfactant and oil mixture. Once separated from the sand, the oil can be separated from the proteins using tangential flow filtration.

Further, the natural protein can be reconstituted and used again, dramatically reducing costs while increasing efficiency. The oil and protein can be separated using a tangential flow filtration apparatus, which can allow the protein to be separated and reused to once again bind oil from the tar sands. The proteins can continually be used until the proteins denature. The foam is also biodegradable, which is ideal for use in this process, reducing environmental impact.

Agricultural Application

Another embodiment of the present disclosure involves application of the surfactant protein to plants. In various embodiments, the protein surfactant of the present disclosure, when sprayed on plants, can have the tendency to "cling" to the leaves and stems. When mixed with nutrients/water, the present disclosure can increase the time to allow for the absorption of nutrients into the plant permitting accelerated growth. For example, the organic surfactant used is very viscous, which limits the overall evaporation of the liquid on the leaves and stems.

Furthermore, the "clinginess" of the surfactant can enhance efficacy of insecticides/pesticides because, the organic surfactant, being very viscous, can remain on the leaves and stems to provide a coating that can prevent any pesticides from being washed off. Application of the surfactant allows farmers to use less water, and less insecticides/pesticides, and is biodegradable, saving resources and presenting an environmentally sound alternative to existing practices.

Living Tissue Transportation Application

An additional embodiment of the present disclosure uses the surfactant foam in order to improve the transportation of organs and other living tissue. This application can aid in the prevention of any bacteria accumulating on any organ tissues during transport. Additionally, this application can allow for the organ tissue to be coated with an organic viscous protectant that will not harm the cells in transport.

Further, according to this embodiment, the surfactant foam of the present disclosure is antibacterial. The antibacterial nature of the foam as well as the ease of gas exchange, and maintenance of moisture content, all provide an ideal protectant for the maintenance and transportation of organs.

Food Transport Application

The incorporation of the synthetic surfactant improves upon the methods described in U.S. App. No. 2018/0213807. The organic surfactant of the present disclosure can aid in the increased freshness of the living transportation of foods that are subject to spoilage. The increased length of time in shipping as well as the reduced weight in shipping purely foam, rather than any other liquids and gasses, such as water for seafood, will greatly enhance the profits of the shipping industry. This process can entail filling a shipping container with foam where the food of interest will be placed and shipped. This process can be used for any food type where spoilage is a concern.

The application involves the live transportation of crustaceans as well as other foods where spoilage and freshness are key considerations. In some embodiments, fresh crustaceans or other seafood are placed into a suitable receptacle at least partially filled with a foam composition including the surfactant foam described herein, a gas and an aqueous carrier. In some embodiments, the method is performed as an intermediate storage or packaging operation, prior to final packaging for or bulk provision to the consumer.

Methods

Sample Acquisition

Figure 2:
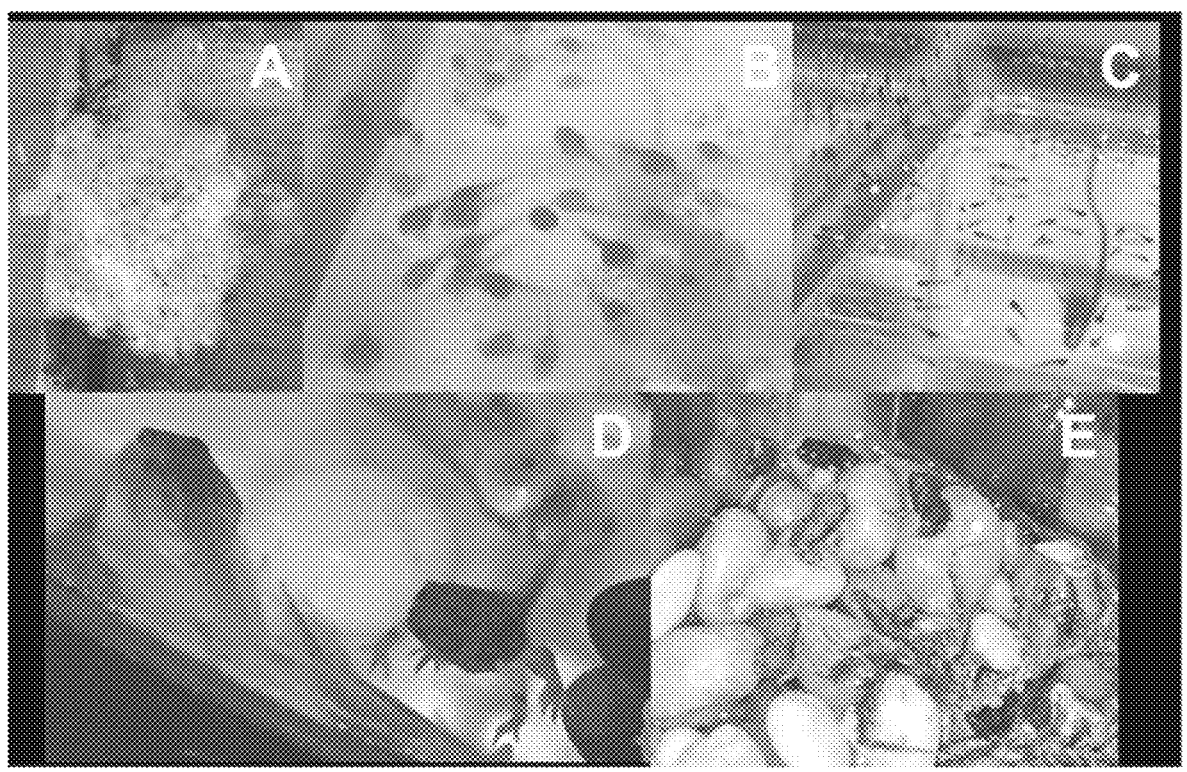
FIG. 2 shows various images of a foam nest, tadpoles and frogs.

Samples of frog foam were acquired from a colony of Túngara frogs at Pacific University in Marcos Gridi-Papp's laboratory. This laboratory supplied one foam nest that was used to characterize the molecules in the foam. The foam was frozen and lyophilized to preserve the foam for future studies. The eggs were allowed to hatch and the tadpoles were housed in a 25° C. water tank until the tadpoles metamorphosed. Once metamorphosis was completed, the frogs were placed in a tank with rocks and moss, allowing further nest formation for future studies (FIG. 2). The foam was then reconstituted in water. The glycoproteins were separated into proteins and carbohydrates using 10% TCA in water. The sample was left overnight and the proteins separated from the carbohydrates and precipitated out of the solution. The remaining liquid containing the carbohydrates was then frozen and lyophilized. The powder remaining was then placed in an ethanol solution to remove any potential contaminates from the carbohydrates. The separated proteins and carbohydrates were then lyophilized and stored for future studies.

Carbohydrates Study

After lyophilizing, the carbohydrates were dissolved again into an 80:20 acetonitrile:water solution. The solution was then placed onto a MALDI plate for analysis by placing 1 μl of sample onto the plate. Once the sample was dried a solution of 10 mg/ml 2,5-dihydroxybenzoic acid was used as a matrix by placing 1 μl on top of the dried sample. A Thermo LTQ Orbitrap mass spectrometer with MALDI inlet was run from 1000-2000 m/z. Peaks correlating to the carbohydrates were then fragmented to identify the structure of the polysaccharide.

Proteins Study

The lyophilized proteins collected were dissolved into a 100 mM ammonium bicarbonate buffer with 8M urea. A 0.5 M solution of dithiothreitol (DTT) was then added to make a final concentration of 5 mM DTT in solution. The mixture was then left at 56° C. for 45 minutes. The solution was then cooled to room temperature and diluted 1:5 with 25 mM ammonium bicarbonate. A 0.1 M calcium chloride solution was then added to the mixture to form a final concentration of 1 mM calcium chloride. Then trypsin was added at a concentration of 5 ug/ml and incubated at 37° C. overnight. The solution was then let cool to room temperature and the digestion was stopped by acidification with 0.4% trifluoroacetic acid. The samples were then cleaned using a C18 ZipTip and were analyzed using a Waters Synapt G2 HD-MS mass spectrometer.

Results

Carbohydrates Results

Figure 3:
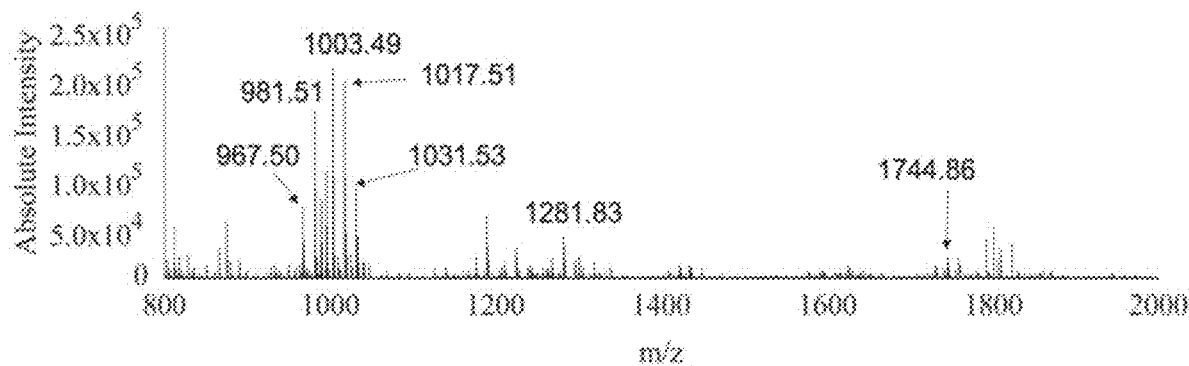
FIG. 3 shows a foam polysaccharide mass spectrum analysis chart.
Figure 4:
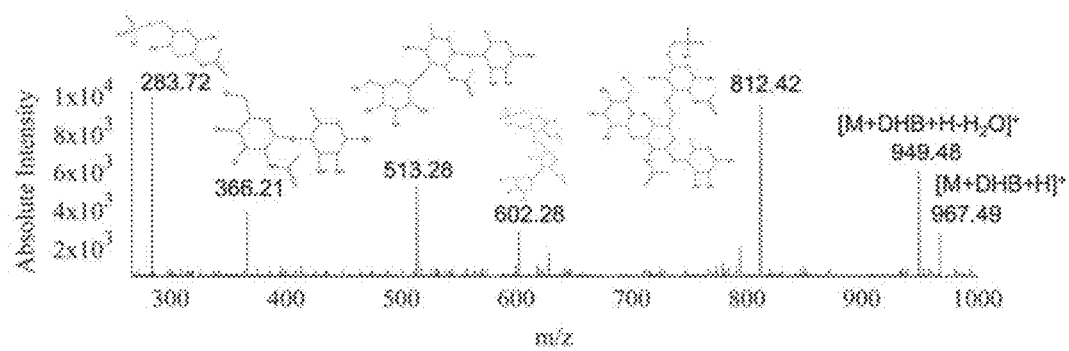
FIG. 4 shows the fragmentation pattern of a tetrasaccharide in a mass spectrum analysis chart.

Carbohydrate peaks were found at m/z 967.50, 981.51, 1003.49, 1017.51, 1031.53, 1281.83, and 1744.86 (FIG. 3). These peaks were each fragmented and analyzed to determine the carbohydrate structure. The peak at m/z 967.50 was an [M+Matrix+H]+ ion and fragmented to m/z 812.42, 602.28, 513.28, 366.21, and 283.72, was found to be a tetrasaccharide. The peak at m/z 812.42 was found to be the tetrasaccharide with no matrix. The peak at m/z 602.28 was due to a loss of water and loss of the fucose. The peak at m/z 513.28 was due to the loss of the 6-sulfonate-n-acetyl-galactosamine. The peak at 366.21 was due to a loss of the 6-sulfonate-n-acetyl-galactosamine and a loss of the galactose and the peak at m/z 283.72 was due to a peak from the 6-sulfonate-n-acetyl-agalactosamine with a loss of water. The tetrasaccharide was attributed to a fucose, bound via an α1-4 to an n-acetyl-galactosamine. This n-acetyl-galactosamine had a 6-sulfonate-n-acetyl-galactosamine bound via a β6-3. The n-acetyl-galactosamine also had a galactose bound via a β1-3 linkage (FIG. 4).

Figure 5:
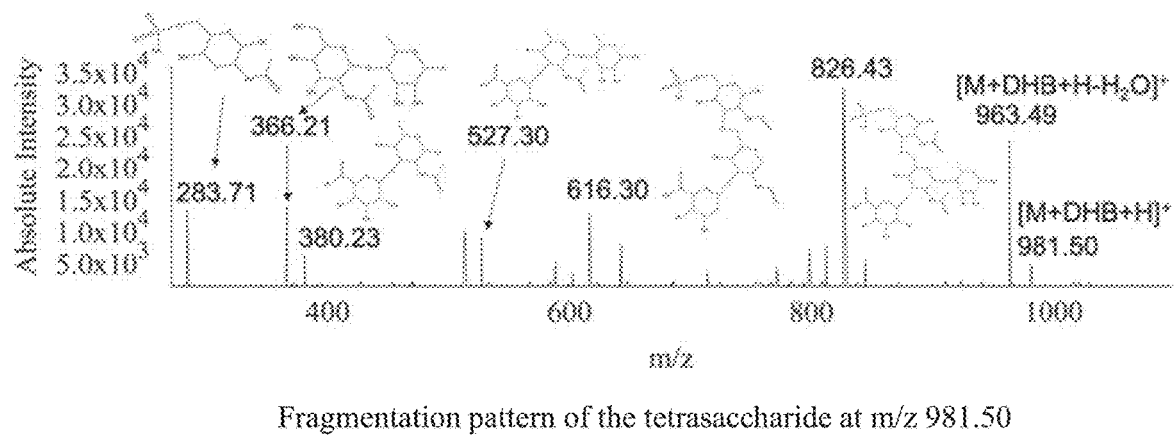
FIG. 5 shows the fragmentation pattern of a tetrasaccharide in a mass spectrum analysis chart.

The peak at 981.50 was an [M+Matrix+H]+ ion was associated with another tetrasaccharide with the tetrasaccharide being m/z 826.43. The m/z 981.51 ion fragmented to m/z 963.49, 826.43, 616.30, 527.30, 380.23, 366.21, and 283.71 (FIG. 5). This tetrasaccharide was found to be the result of an n-acetyl-galactosamine via an α1-3 bond, a uronic acid bound via a β1-3 and a 6-sulfonate-n-acetyl-galactosamine at the β6-3 position. The m/z 963.49 peak was associated with a loss of water from the matrix adducted tetrasaccharide. The m/z 826.43 peak was the ion for the tetrasaccharide. The m/z 616.30 peak was associated with a loss of the fucose. The m/z 527.30 peak was a result of the loss of the 6-sulfonate-n-acetyl-galactosamine. The m/z 380.23 peak is associated with a loss of the fucose and the 6-sulfonate-n-acetyl-galactosamine. The m/z 366.21 peak is associated with the loss of the uronic acid and the 6-sulfonate-n-acetyl-galactosamine. The 283.71 peak is associated with 6-sulfonate-n-acetyl-agalactosamine with a loss of water.

Figure 6:
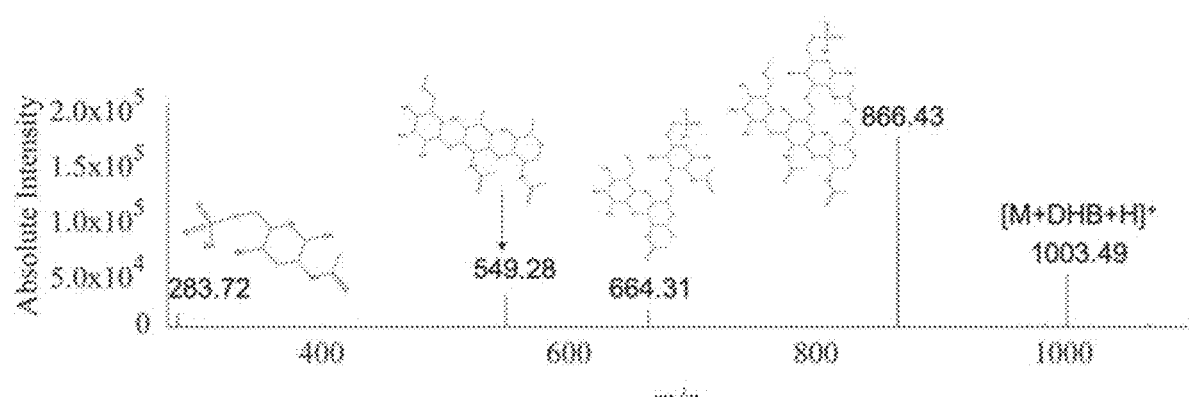
FIG. 6 shows the fragmentation pattern of a tetrasaccharide in a mass spectrum analysis chart.

The peak at m/z 1003.39 was an [M+Matrix+H]+ ion and fragmented to m/z 866.43, 664.31, 549.28, and 283.72, which was found to be a another tetrasaccharide (FIG. 6). This tetrasaccharide was composed of an n-acetyl-galactosamine bound to another n-acetyl-galactosamine via a β1-3 linkage. A methylated galactosamine was bound to the center n-acetyl-galactosamine by a β1-3 linkage. A 6-sulfonate-n-acetyl-galactosamine was bound to the central n-acetyl-galactosamine by a β6-3 bound. The peak m/z 866.43 was the tetrasaccharide without the matrix adduct. The m/z 664.31 was a result of a loss of an n-acetyl-galactosamine, while the m/z 549.28 peak was a result of a loss of the 6-sulfonate-n-acetyl-galactosamine. The m/z peak at 283.72 was a result of only the 6-sulfonate-n-acetyl-galactosamine.

Figure 7:
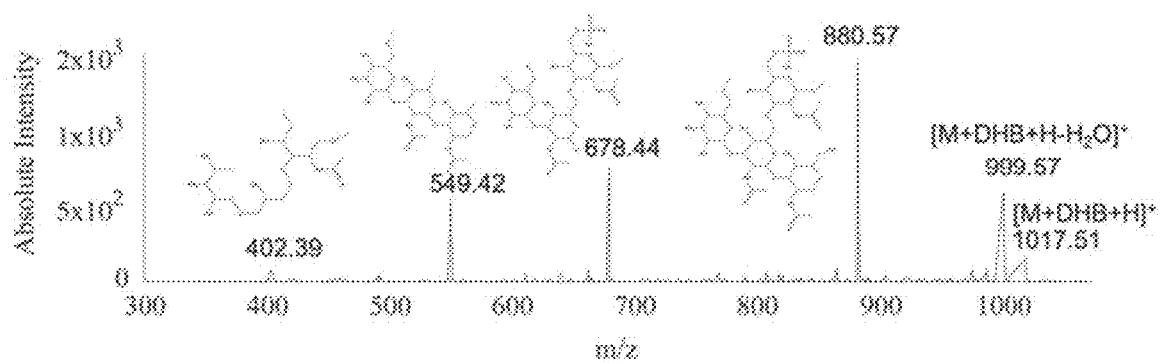
FIG. 7 shows the fragmentation pattern of a tetrasaccharide in a mass spectrum analysis chart.

The peak at m/z 1017.51 was found to be the last tetrasacharide in the sample and it was found to be composed of an n-acetyl-galactosamine bound via a 1-3 linkage to a central n-acetyl-galactosamine. There is a galactosamine bound to the central n-acetyl-galactosamine bound via a β1-3 linkage. There is also a 6-sulfonate-n-acetyl-galactosamine bound via a 36-3 linkage to the central n-acetyl-galactosamine (FIG. 7). The m/z 1017.51 peak fragmented to m/z 999.57, 880.57, 678.44, 549.42, and 402.39. The 999.57 was a result of the ion with a matrix adduct and a loss of water. The m/z 880.57 peak was the tetrasaccharide without the matrix adduct. The m/z 678.44 peak was due to a loss of the n-acetyl-galactosamine bound via the β1-3. The m/z 549.42 peak was a result of a loss of the 6-sulfonate-n-acetyl-galactosamine at the β6-3 linkage. The m/z 402.39 peak was due to a loss of multiple water molecules from the 549.42 peak.

Figure 8:
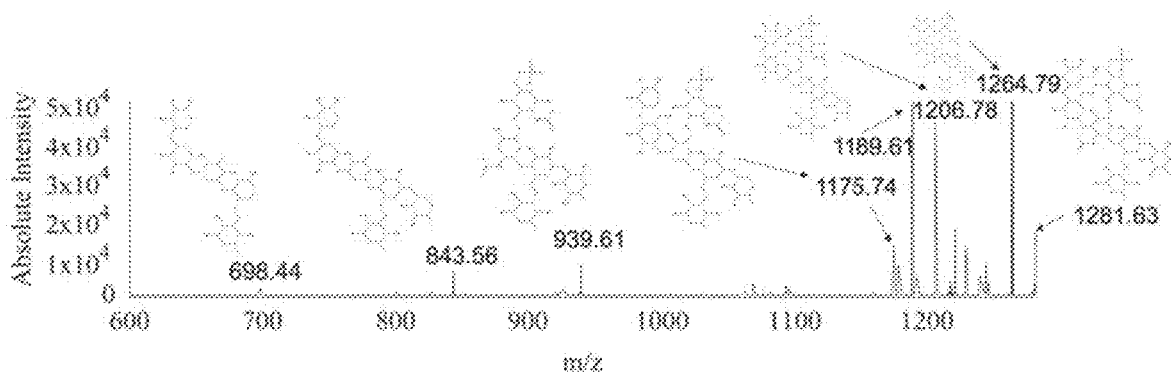
FIG. 8 shows the fragmentation pattern of a polysaccharide in a mass spectrum analysis chart.

Larger polysaccharides were found at m/z 1281.63 and 1744.84. These compounds were a result of a heptasaccharide and a nonasaccharide. The heptasaccharide contained two fucose molecules bound to a galactosamine via a α1-2 and an α6-3 bond. The galactosamine was bound to a n-acetyl-galactosamine via a β1-2 linkage. The n-acetyl galactosamine had a 6-sulfonate-n-acetyl-galactosamine and a galactose molecule bound via a β6-3 and a β3-1 linkage, respectively. The galactose further had another galactose bound via a 134-1 linkage. This ion at m/z 1281.63 fragmented to m/z 1264.79, 1206.78, 1175.74, 939.61, 843.56, and 698.44 (FIG. 8). The m/z peak at 1189.61 was a result of the instrument and did not resemble the actual sample. The m/z 1264.79 peak was due to a loss of a water molecule from the parent ion. The m/z 1206.78 peak was a result of a loss of the n-acetyl group and a loss of water from the parent ion. The m/z 1175.74 peak was due to a loss of the methoxy group from the ion at m/z 1206.78. The m/z 939.61 peak occurred because of a loss of the two galactose molecules from the n-acetyl galactosamine. The 843.56 peak was resulted from a loss of the 6-sulfonate-n-acetyl-galactosamine. The m/z 698.44 peak was due to a loss of one of the fucose molecules and a loss of the 6-sulfonate-n-acetyl-galactosamine.

Figure 9:
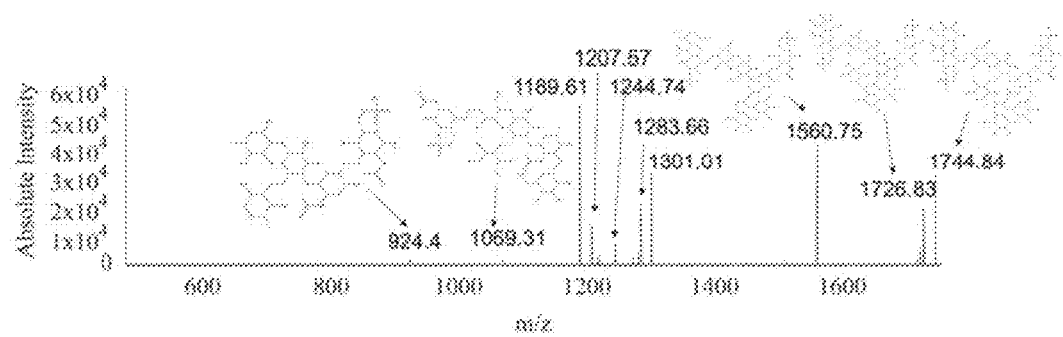
FIG. 9 shows the fragmentation pattern of a polysaccharide in a mass spectrum analysis chart.

The m/z peak at 1744.84 was attributed to a nonasaccharide comprised of a galactose bound another galactose bound via a β1-3 linkage. The galactose is again bound to a n-acetyl-galactosamine via a β1-3 linkage. The n-acetyl galactosamine has another 6-sulfonate-n-acetyl-galactosamine bound via a β6-3 linkage. The n-acetyl-galactosamine has a third saccharide bonded to it at the 1 position and it is bound to a galactose. This galactose is bound to a fucose and another galactose via an α6-3 bond and a β1-2 bond, respectively. This bonded galactose has a 6-sulfonate-n-acetyl-galactosamine bound via a β6-4 linkage and the 6-sulfonate-n-acetyl-galactosamine has a galactose bound via a β3-1 bond (FIG. 9). This parent ion fragmented to m/z ions 1726.82, 1560.75, 1069.31, and 924.4. Other ions existed as a result of the instrument at m/z 1189.61, 1207.57, 1244.74, 1283.66, and 1301.01. The m/z peak at 1726.83 was due to a loss of water from the parent ion. The m/z 1560.75 peak was due to a loss of one of the fucose molecules. The m/z 1069.31 was due to a loss of the 6-sulfonate-n-acetyl-galactosamine and a loss of a galactose molecule and loss of water. The m/z 924.40 peak was due to a loss of three galactose molecules, a 6-sulfonate-n-acetyl-galactosamine molecule. After analysis was completed, a total of 6 polysaccharides were found that are used in the glycoprotein structure of the Túngara frog foam.

Protein Results

Figure 10:
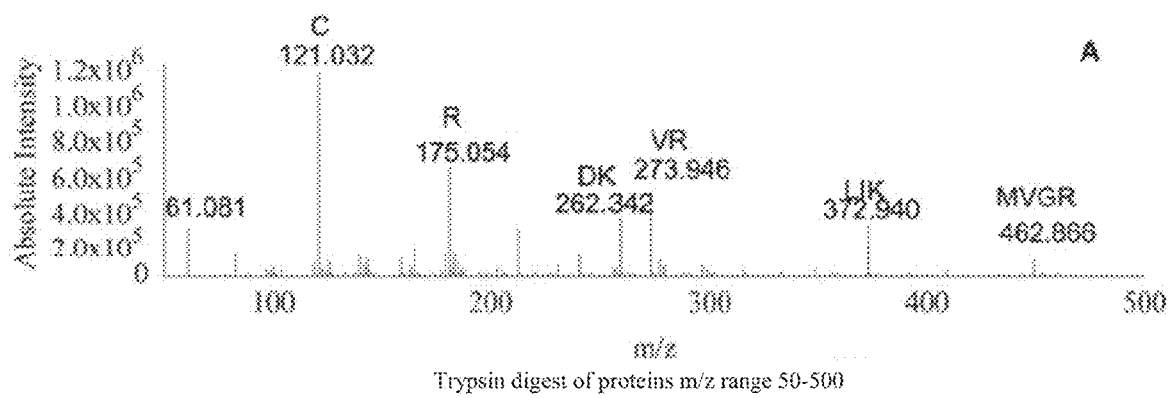
FIGS. 10 and 11 show a mass spectrum analysis chart with respect to trypsin digestion of ranaspumin proteins.
Figure 11:
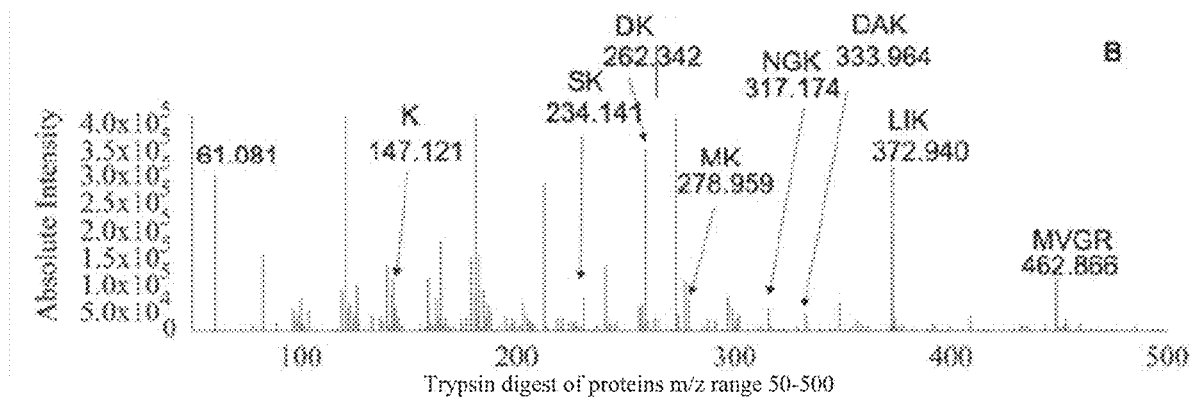

After trypsin digestion, the protein samples were run to ensure the ranaspumins were present in the foam as previously reported. The protein samples run resulted in the finding of protein fragments at m/z values of 462.866, 372.940, 333.964, 317.174, 278.959, 273.946, 262.342, 234.141, 175.054, 147.121, and 121.032. These m/z values correspond to protein fragments of MVGR, LIK, DAK, NGK, MK, VR, DK, SK, R, K, and C (FIG. 10). The fragments identified allow for accurate determinations of Rsn-1, Rsn-2, Rsn-3, Rsn-4, Rsn-5, and Rsn-6.

Conclusion

Figure 12:
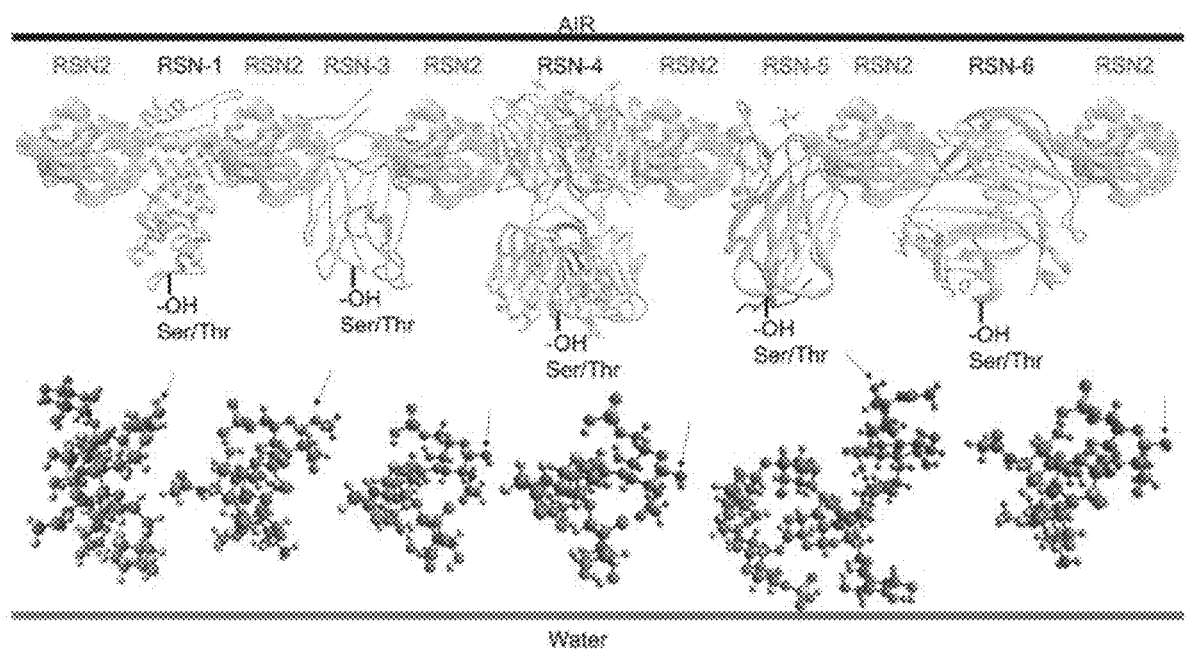
FIG. 12 illustrates a proposed Túngara frog foam nest glycoprotein structure including surfactant proteins (RSN-2, RSN-3, and RSN-5) and binding proteins (RSN-1, RSN-4 and RSN-6).

The Túngara frog foam collected could be characterized given the methods described above. The carbohydrates discovered in this project were all analyzed and fragmented to determine the structures of each polysaccharide. The proteins were also confirmed from previous reporting that the ranaspumin proteins are the main proteins in the foam nest. The polysaccharides consisted of 4 tetrasaccharides, a heptasaccharide and a nonasaccharide. The saccharides all contain at least one free hydroxyl group to bind to the ranaspumins via a serine or threonine amino acid. The ranaspumins all contained one or more serine or threonine for binding via an F-type fucolectin. The proposed layout of the foam structure can now be enhanced from the Cooper research group to include all the polysaccharides in the foam, this is the last step in characterizing the Túngara frog foam nest (FIG. 12).

Given the structures of the polysaccharides and the already-sequenced proteins, the glycoprotein composition is characterized. The next step in the recreation of the foam artificially will be to determine the bonding location of the carbohydrate to the protein. This can be done using computational chemistry with the crystal structures of the proteins. Unfortunately, the crystal structures of all ranaspumins are not yet characterized. Further research should be conducted to determine the crystal structure of all the ranaspumins. However, until the crystal structure of the ranaspumins can be found, surrogates to these ranaspumins that are commercially available would be a potential option to simulate and synthesize the foam artificially until a crystal structure can be found for all the ranaspumins.

Once the surrogates have been simulated and acquired, the polysaccharides can be synthesized. The synthesis of polysaccharides is challenging, however combining two polysaccharides synthesis routes into one route would allow for a decreased overall synthesis time. This will bring the total synthesis time per tetrasaccharide from 20 hours per addition of a monosaccharide to the chain down to 10-12 hours per addition of a monosaccharide to the chain[12-14]. This will decrease the overall time it would take to synthesize the polysaccharides and allow for the glycoprotein to be synthesized.

EXPERIMENTS

Application of Ranaspumin Protein Mix (RSN1-6) as Pesticide Adjuvant

Agricultural adjuvants or pesticide adjuvants are broadly classified as any substance added to the spray tank, separate from the pesticide formulation that will improve the performance and/or the efficacy of the pesticide. This can include everything from chemicals that improve the retention of the pesticide on the leaves to wetter-spreaders to feeding stimulants.

Aim of the Experiment

Ranaspumin proteins are known to possess surfactant properties in addition to having antimicrobial, antipathogenic properties[15]. The aim of this experiment was to test whether the surfactant property of the proteins will help to increase the efficacy of the pesticide and/or increase the retention of the pesticide in the leaves after its application.

Figure 13:
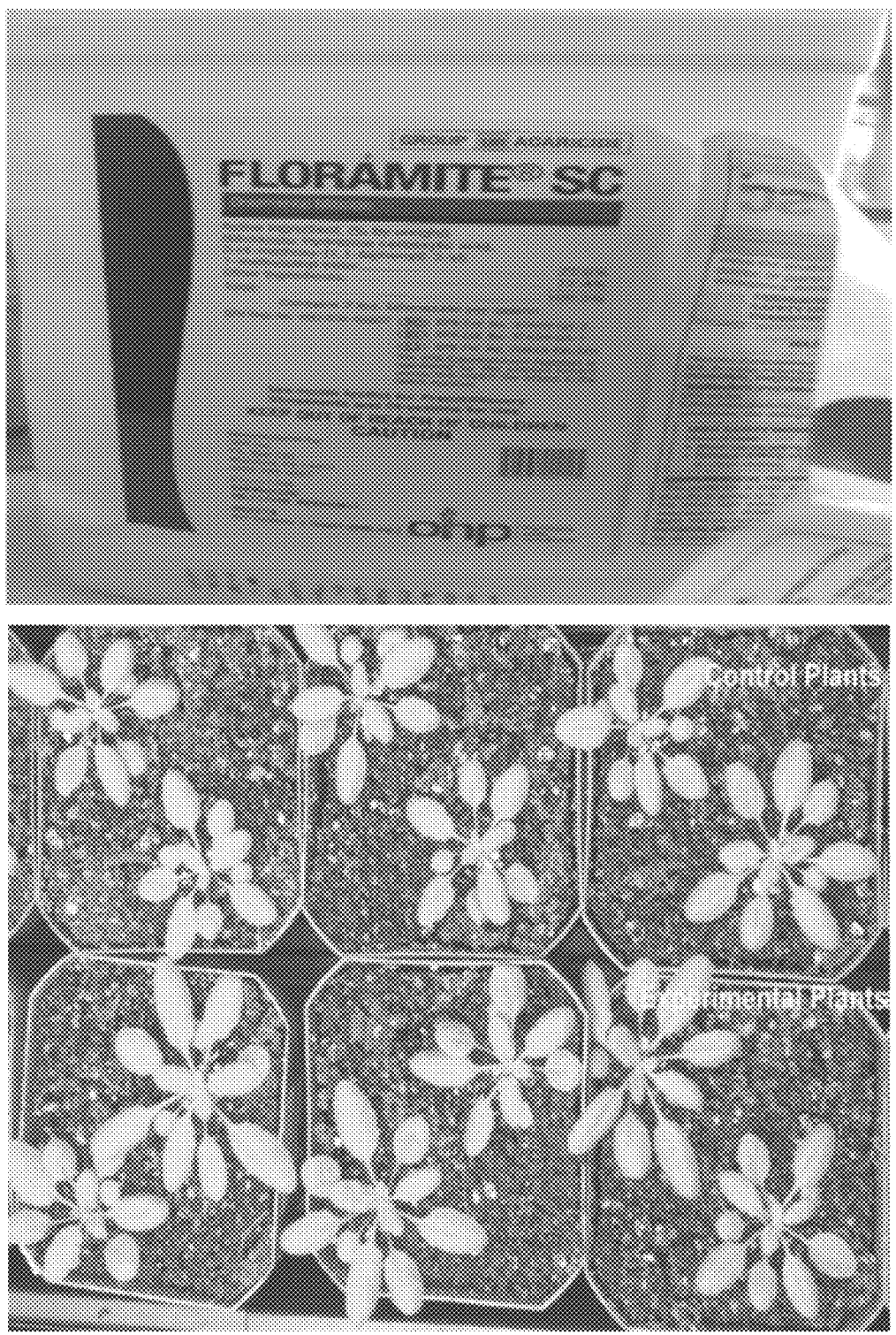
FIG. 13 shows 12 four-week-old *Arabidopsis thaliana* (columbia ecotype) plants treated with Floramite®.

Experimental Setup 12 four-week-old *Arabidopsis thaliana* (columbia ecotype) plants were used for the experiment. (6 control, 6 experimental) (FIG. 13).

Growth condition: plants were grown in soil at in 16-hour days/8-hour nights light cycle with temperatures of 22° C. Lighting was provided with fluorescent bulbs giving an average light intensity of 175 micromoles/meter$^2$ second. Seeds were cold treated (stratification) for 3 days at 4° C. after imbibition to synchronize germination The experimental plants were applied with a mixture of Floramite® and RSN 1-6 mixture (50 μL of 10 mg/mL) directly to the leaves using a pipette. The control plants were applied with just the pesticide. Samples were collected at the end of 5 days and 10 days.

Figure 14:
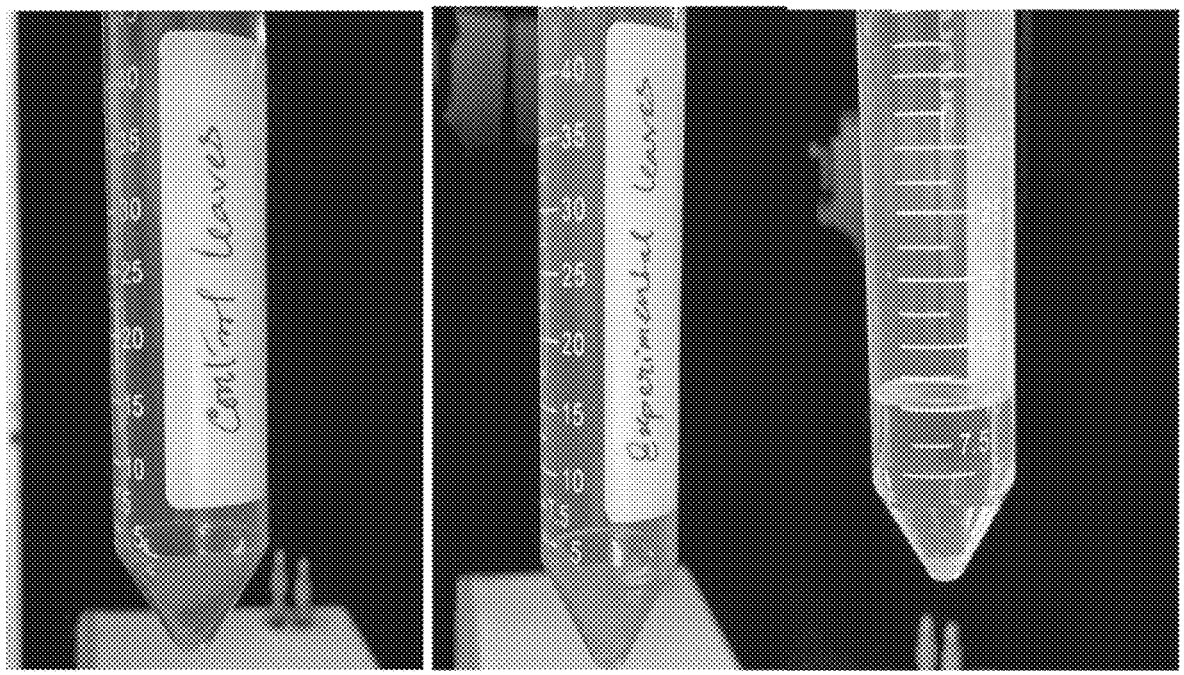
FIG. 14 shows homogenized control and experimental leaves of *Arabidopsis thaliana* (columbia ecotype) plants treated with Floramite®.

Collection of Leaf Samples and Extraction Method 4 control leaves and 4 experimental leaves were collected at the end of 5 days and 10 days of application. The leaves were homogenized using liquid nitrogen and extracted using Methanol:Chloroform mix (2:1) (FIG. 14). The aqueous phase was collected for GC/MS analysis. A 0.01 mg/mL caffeine solution was used as an internal standard.

GC/MS Analysis

A GC/MS instrument (Thermo Focus GC, Polaris ion trap MS) with a DB-5 column was used for quantification of the pesticide. Helium was used as the carrier gas with a constant flow of 1 mL/min. The oven temperature started at 75° C. and remained at the temperature for 3 mins increasing to 120° C. at 25° C./min ramp rate and then increased to 300° C. at 5° C./min ramp rate, holding at 300° C. for 11 min. Injection port was adjusted 250° C. and splitless mode injection was used. The MS transfer line was kept at 200° C. with a mass range of m/z 0-650 being set for the run.

Results

The data from GC/MS runs performed for the control and experimental leaf samples are tabulated below. The concentrations of Bifenazate for the control and experimental samples were calculated to compare the difference in retention of the pesticide in the leaves from the two setups.

Figure 15:
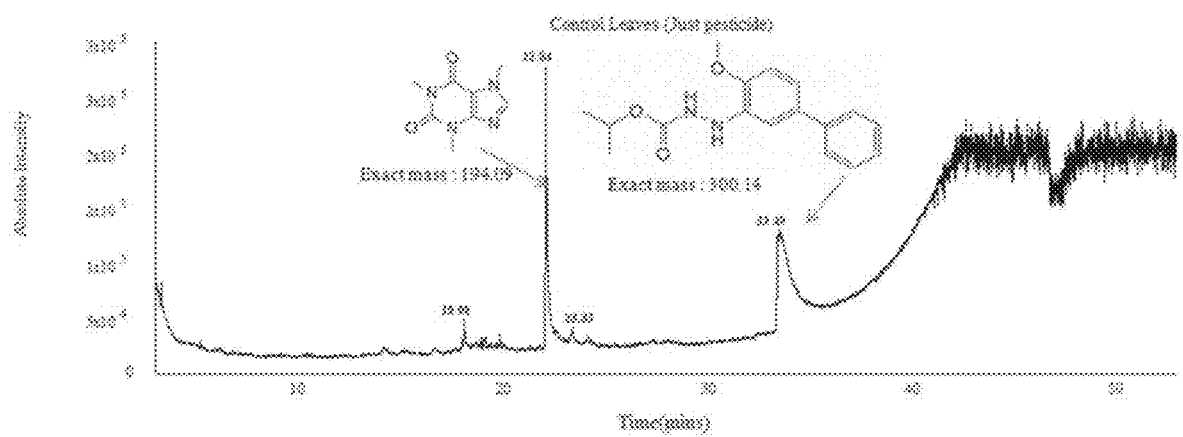
FIG. 15 shows a chromatogram of a GC/MS run of control leaf samples after 5 days. The peak at 22.04 mins represents an internal standard peak for caffeine and the peak at 33.49 mins represents a peak for the pesticide.
Figure 16:
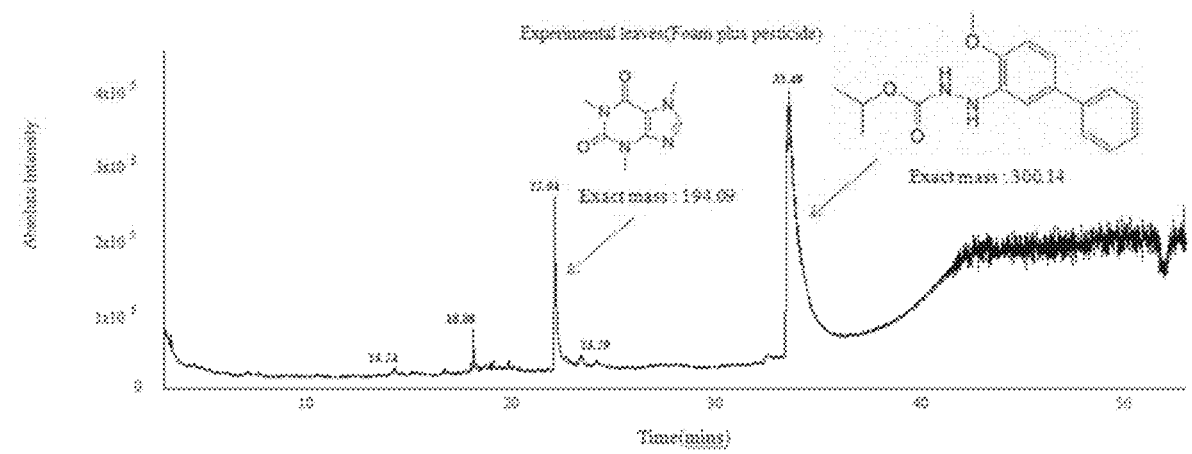
FIG. 16 shows a chromatogram of a GC/MS run of experimental leaf samples after 5 days. The peak at 22.04 mins represents an internal standard peak for caffeine and the peak at 33.49 mins represents a peak for the pesticide.

Concentration of Bifenazate in control leaf sample –0.018 μg/μL (FIG. 15). Concentration of Bifenazate in experimental leaf sample –0.065 μg/μL (FIG. 16). Concentrations were calculated using the peak area of the internal standard compared to the peak area of the pesticide. The experimental leaf was calculated to have a 3.6 times the amount of Bifenazate when compared to the control leaf.

Figure 17:
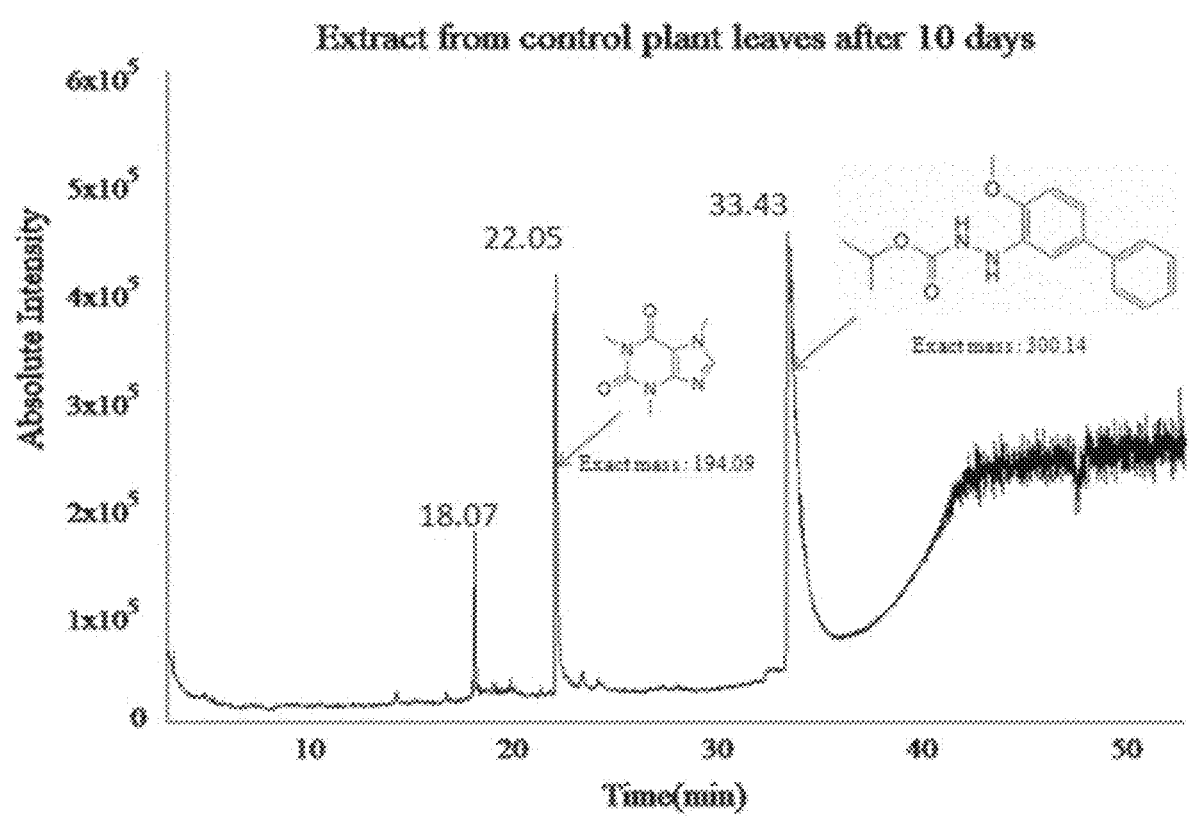
FIG. 17 shows a chromatogram of a GC/MS run of control leaf samples after 10 days. The peak at 22.05 mins represents an internal standard peak for caffeine and the peak at 33.43 mins represents a peak for the pesticide.
Figure 18:
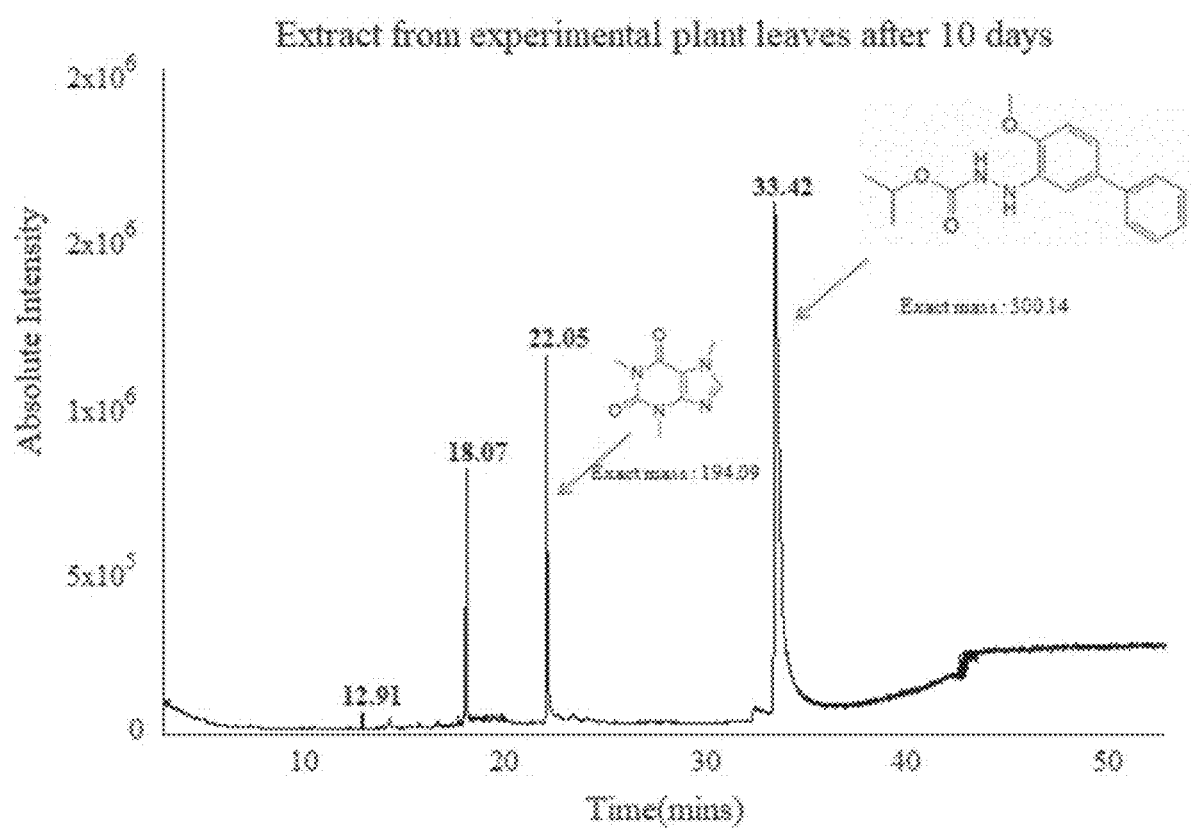
FIG. 18 shows a chromatogram of a GC/MS run of experimental leaf samples after 1 days. The peak at 22.05 mins represents an internal standard peak for caffeine and the peak at 33.42 mins represents a peak for the pesticide.

Concentration of Bifenazate in control leaf sample (after 10 days) –0.321 μg/μL (FIG. 17). Concentration of Bifenazate in experimental leaf sample (after 10 days) –0.403 μg/μL (FIG. 18). All concentrations were calculated using the peak area of the internal standard compared to the peak area of the pesticide. The experimental leaf was calculated to have 1.2 times the amount of Bifenazate when compared to the control leaf Conclusion Samples collected at the end of 5 days and 10 days of the experiment shows higher concentration of pesticide in the sample extracted from the leaves which were applied with the foam and pesticide mix compared to the sample collected from the leaves applied with just the pesticide. This might be an indication of the fact that the foam is acting as an adjuvant for the pesticide and helping it in a better absorption in the leaves and/or it's helping it to adhere to the leaves in a more effective way.

Application of Ranaspumin Protein Mix (RSN1-6) as an Extraction Method for Tar-Sand Currently the extraction method for Tar-Sand is the use of an inorganic solvent such as dichloromethane (DCM). With the use of an organic solvent such as Ranaspumin protein, with the aid of a Tangential Flow Filtration system (TFF), aromatic compounds can be extracted from the hydrocarbons found in Tar-Sands.

Aim of Experiment

Ranaspumin proteins are known to be surfactants. Not only have inorganic solvents been used to extract oil from Tar-Sands, but surfactants have been used as a clean alternative to inorganic solvents.[15] With the use Ranaspumin, the aromatics and hydrocarbons will separate from the Tar-Sand and the Ranaspumin will provide a more efficient amount of extraction when compared to the inorganic method of DCM.

Experimental Step-Up 2 mg of Tar-Sand (Athabsca) were split into 1 mg portions and placed into two separate vials containing 1 mL of DCM and 1 mL of RSN 1-6. The samples were vortexed for 20 minutes, 10 μL of the vortexed sample of DCM was placed into 990 μL of hexane. The sample containing the RSN mixture was then extracted using hexane, the hexane layer was then stored into a glass vial. 10 μL of sample was placed into 990 μL of hexane and both samples were run on a GC-MS. The remaining RSN mixture was run though the TFF system.

Tangential Flow Filtration System (TFF)

Figure 19:
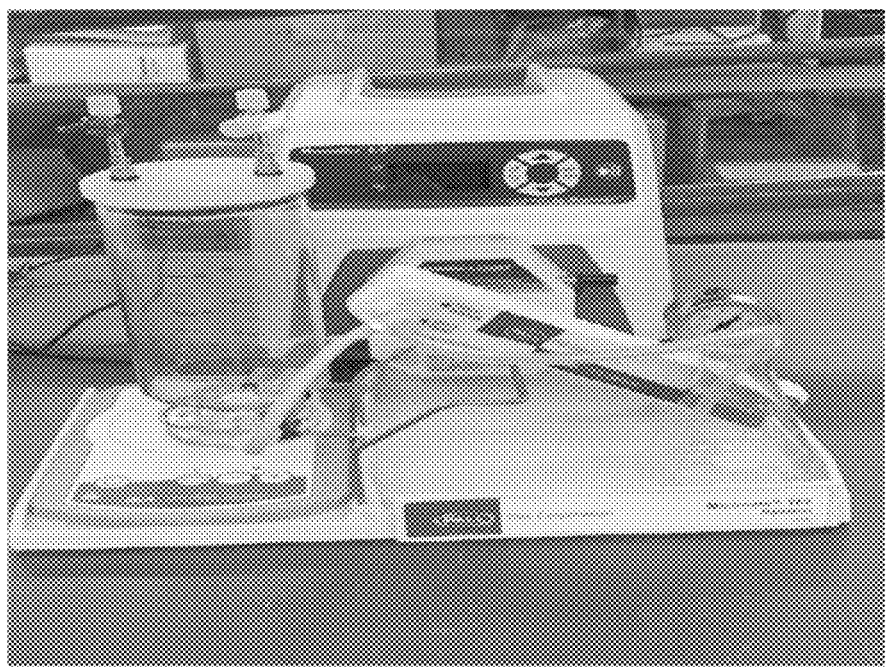
FIG. 19 shows a tangential flow filtration system.

To run the TFF system (FIG. 19) sample containing the protein and oil will be added into the reservoir with a minimum volume of 1.7 mL. The pump then pushes the sample through the system with an optimal flow rate of 30 mL/minute to 40 mL/minute until the sample approaches the capsule. Once the sample reaches the capsule, the protein will be separated from the oil that is extracted from the Tar-Sands. The sample will run continuously through the system a minimum of 3 passes to increase the percent of removal of protein form the oil. The oil will be collected as the first product from the TFF system. A retrieval procedure is run to re-collect the isolated protein from the capsule. Both product recovery and the first product were run on a GC-MS.

GC/MS Analysis

A GC/MS instrument (Thermo Focus GC, Polaris ion trap MS) with a DB-5 column was used for quantification of the Tar-Sand samples. Helium was used as the carrier gas with a constant flow of 1 mL/min. The oven temperature started at 60° C. and remained at the temperature for 3 minutes increasing to 260° C. at 8° C./min ramp rate holding at 260° C. for 3 minutes. The injection port was adjusted to 250° C. and splitless mode injection was used. The MS transfer line was kept at 200° C. with a mass range of m/z 0-350 being set for the run.

Results

Figure 20:
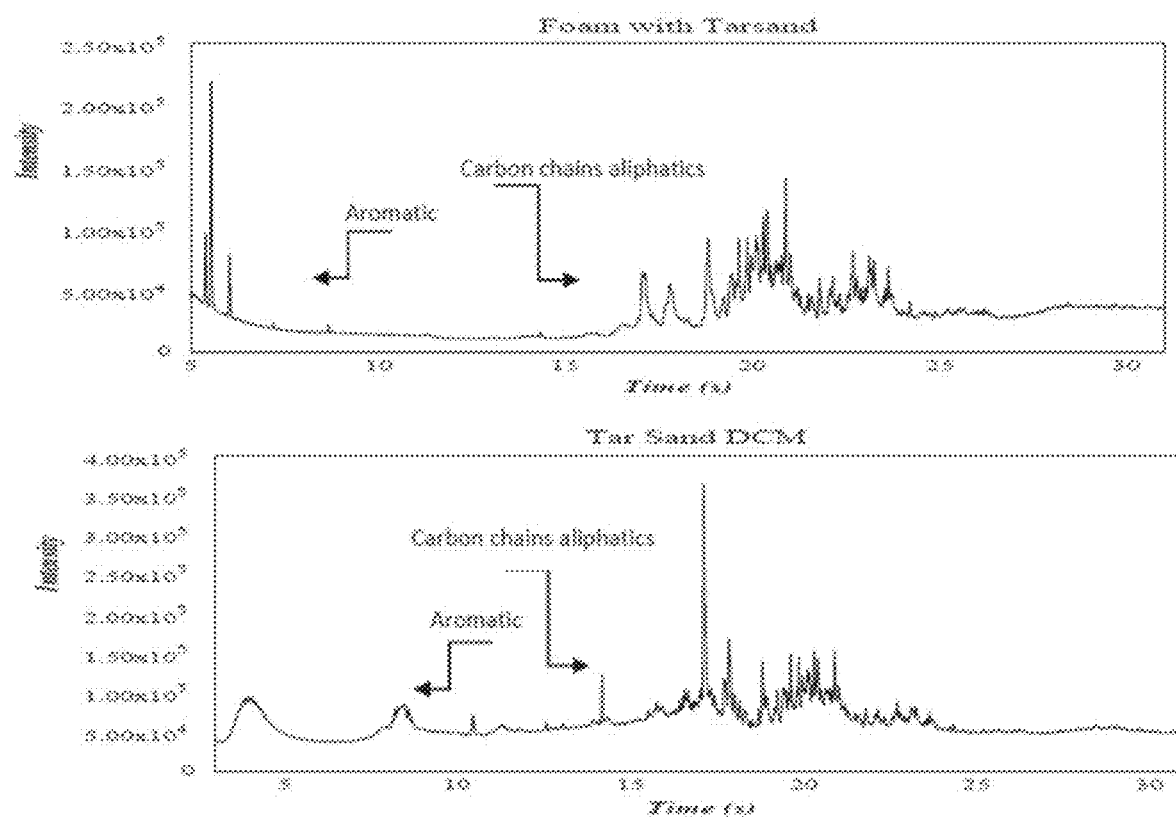
FIG. 20 shows a chromatogram of a GC/DCM (bottom) and RSN mixture (top) showing the aromatic region before 10 minutes and the carbon chains aliphatics between 15-25 minutes.

The data from GC/MS runs were performed for the DCM, RSN mixture before and after being run though the TFF system. The GC run for DCM is shown in FIG. 20 (bottom), and the RSN mixture is shown in FIG. 20 (top) to compare the performance of the RSN mixture.

Figure 21:
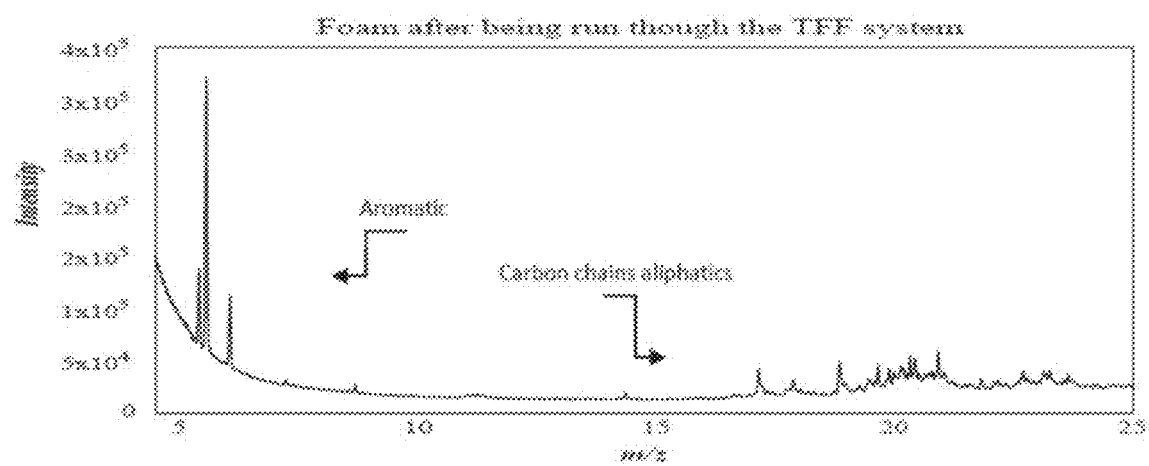
FIG. 21 shows a mass spectrum analysis of an RSN mixture after 3 passes through a tangential flow filtration system. The aromatic region is before 10 minutes and the carbon chains aliphatics is between 15-25 minutes.
Figure 22:
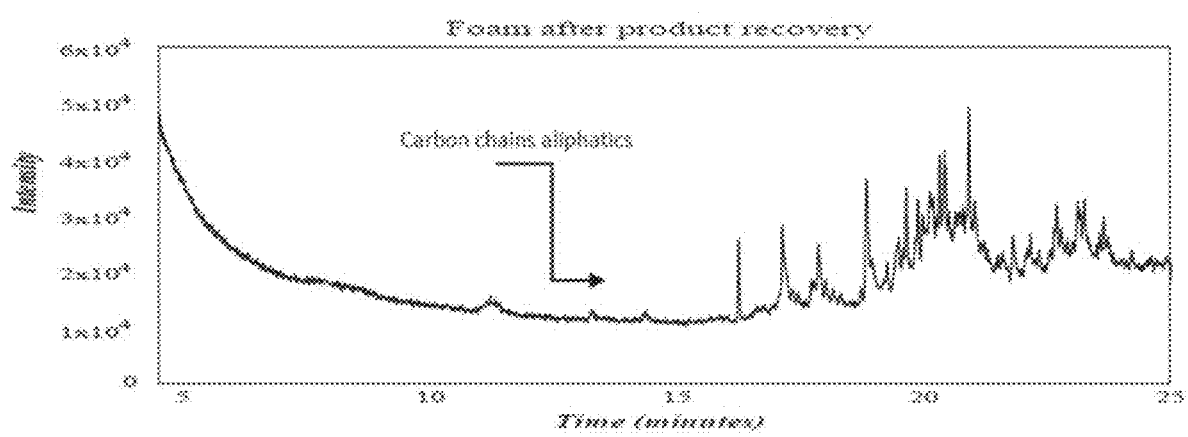
FIG. 22 shows a mass spectrum analysis of an RSN mixture after product recovery performed on a tangential flow filtration system. There is no aromatic region before 10 minutes and the carbon chains aliphatics is between 15-25 minutes.

Once through the TFF, the first product recovery for the RSN mixture GC-MS run is shown in FIG. 21. The final product recovery for the RSN mixture GC-MS run is shown in FIG. 22. After 3 passes though the TFF, the concentration of carbon chain aliphatics decreased roughly by 30%. Once the product recovery protocol was performed, the aromatic region was completely separated of the sample.

Conclusion

The RSN mixture can extract aromatic compounds as well as carbon chains aliphatics. When compared to DCM, the inorganic solvent currently used to extract oil from Tar-Sand, the RSN mixture extracts the same compounds. The RSN mixture can be concluded to be a functioning surfactant for the extraction of oil form Tar-Sands. With the assistance of the TFF system, the RSN mixture sample shows a reduction of roughly 30% for the aromatic compounds and the carbon chains aliphatics, with only three passes through the system. After the product recovery protocol is performed, the aromatic region completely becomes separated from the carbon chains aliphatic region. This can be applied to the use of low aromatic concentrations in high performing gasoline.

Kirby Bauer Antimicrobial Assay on Ranaspumin Protein (RSN1-6)

Antimicrobial agents stop the growth or kill microorganisms such as *Escherichia coli* (*E. coli*). The Kirby Bauer antimicrobial assay or disk-diffusion method is used to test what antibiotic will fight against which bacteria strain.[17] The Kirby Bauer antimicrobial assay, is most commonly used to monitor the growth of bacteria growth around a disk, measuring the radius/diameter of the growth from the disk if a gap is present; this can be done in a time period as short as 24 hours or as long as 5 days.[18]

Aim of Experiment

Ranaspumin proteins are known to possess surfactant properties in addition to having antimicrobial and antipathogenic properties.[15] *E. coli* can be used as the bacteria in a disk-diffusion study to test if ranaspumin proteins have antimicrobial properties against *E. coli* cultures.

Experimental Step-Up

RSN mixture was prepared using equal parts of each protein (RSN 1-6) in a concentration of 10 mg/mL and vortexed until combined.[22] *E. coli* culture plates were prepared and allowed to dry, small filter paper circles were placed on the plate, with a 20 μL of the RSN sample labeled RSN 1-6. RSN mixtures (1-6) and a control were placed onto the filter paper shown in FIG. 23a and FIG. 23b.

Once the protein was placed on the *E. coli* culture plates, the plates were placed into a new Brunswick Scientific Excella E24 Incubator Shaker set at 37° C., for 24 hours. After 24 hours the plates were taken out of the incubator shaker and observed.

Results

RSN 2 and RSN 5 were the only proteins that presented antimicrobial properties. RSN 1, 3-4 and 6 did not show any antimicrobial properties. They can be compared to the control that was run and shown in FIG. 23b. The mixture of RSN 1-6 all in equal parts also showed to have presented without antimicrobial properties even though RSN 2 and 5 were both present with antimicrobial properties. Both RSN 2 and 5 show antimicrobial properties, RSN 2 has a radius of 1.1 cm and RSN 5 has a radius of 0.7 cm of resistance to the *E. coli* colonies. RSN 2 shows high resistance to *E. coli* showing no growth of *E. coli*. colonies near the filter paper disc. While RSN 5 showed moderate resistance to *E. coli*, RSN 5 still had residues of colonies near the filter paper disc.

Conclusion

This demonstrates that unlike RSN 2, RSN 5 slows the rate of the growth of the *E. coli* colonies, while RSN 2 kills the *E. coli* colonies. This can be applied by the applying RSN proteins to antibiotics. Different cultures can be conducted to test if other RSN proteins will show antimicrobial properties with different strains of bacteria.

Denaturing of Ranaspumin Protein (RSN 1-6) Using a Circular Dichromium

Over the past few decades, circular dichromium (CD) has been used to observe the secondary structure of proteins.[19] The α-helix, β-sheets and random coils can all be derived from the CD spectra. α-helix tend to reflect two negative bends round 200-220 nm, f-sheets appear at a negative band at 220 nm and a positive band around 200 nm, and random coils have a positive band at 220 nm and a negative band at 200 nm.[20]

Aim of Experiment

The secondary structure of ranaspumin proteins can be confirmed with CD to identify if there is a presence of an α-helix, f-sheets or random coils. The CD can also be used to monitor the denaturing of a protein structure by observing the intensity of the bands on the spectra. This experiment uses increasing temperature to determine when ranaspumin proteins start to denature in the secondary structure with the use of a CD spectrum.

Experimental Step-Up

A 3 mL solution with a concentration of 0.25 mg/mL of RSN 1-6 was diluted from a range of 2.69 mg/mL-0.50 mg/mL stock solution. The Jasco 815 Circular Dichromium, with Jasco temperature controller and a water bath attachment was used to analyze the RSN 2 protein structure. The initial temperature was set to 20° C., the wavelength was set to 200-300 nm and the temperature was increased by 5° C. after each measurement and allowing for 60 seconds of stability before recording the next measurement, in a temperature range of 20-90° C. A bank was run for a baseline before a 1.5 mL solution was run though the CD and the spectra were monitored for a change in intensity in the bands.

Results

Figure 26:
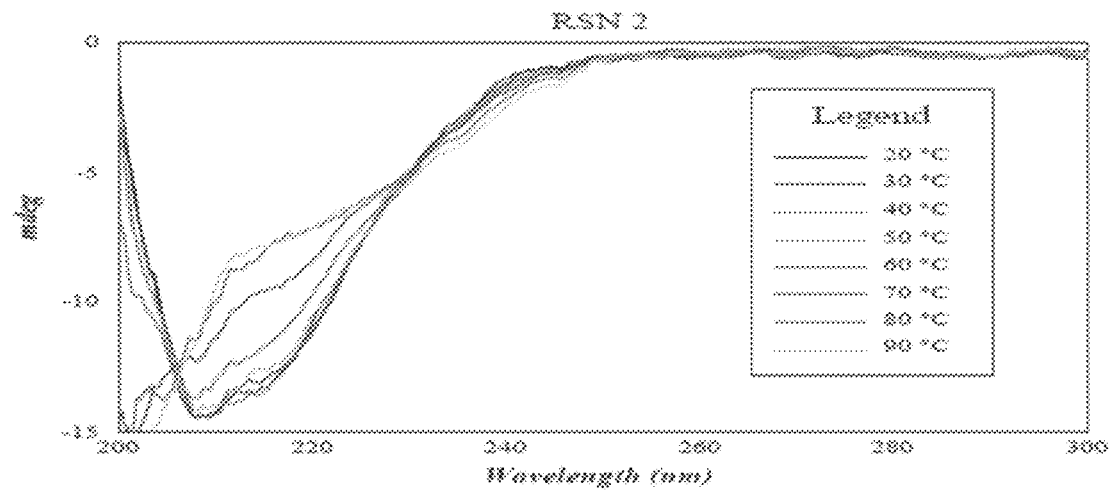
FIG. 26 shows a spectra analysis of denaturing of RSN 2 through a temperature ranging from 20° to 90° C.
Figure 27:
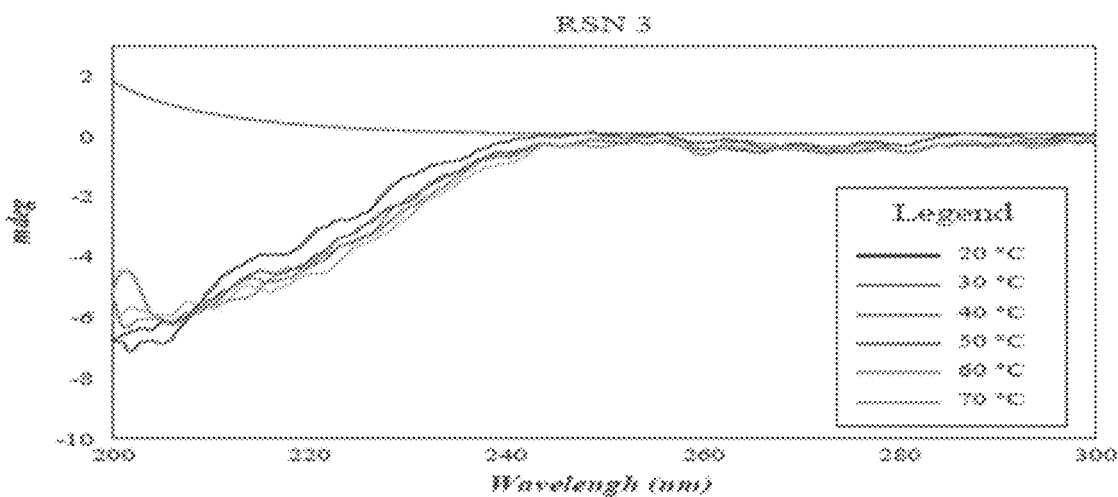
FIG. 27 shows a spectra analysis of denaturing of RSN 3 through a temperature ranging from 20° to 70° C.
Figure 28:
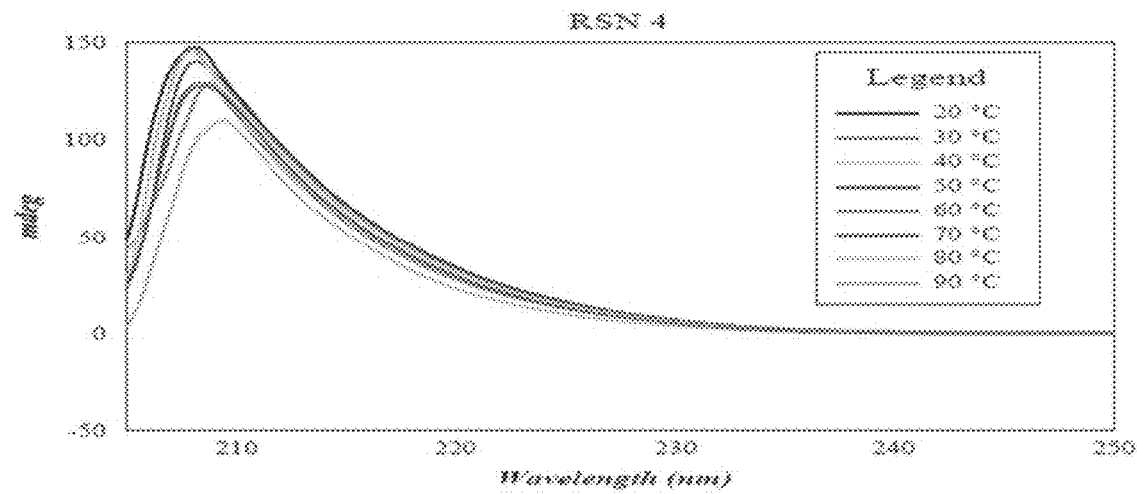
FIG. 28 shows a spectra analysis of denaturing of RSN 4 through a temperature ranging from 20° to 90° C.
Figure 29:
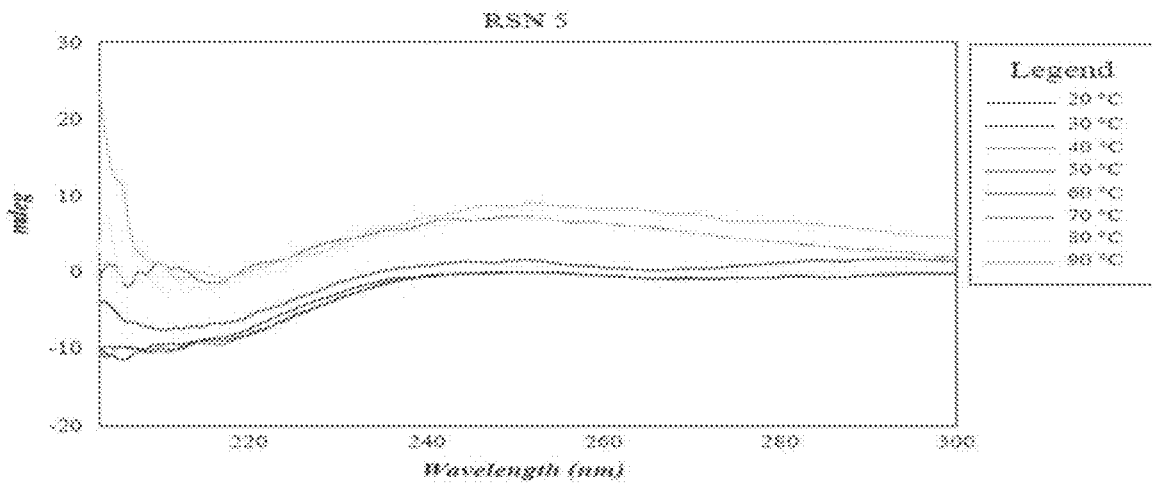
FIG. 29 shows a spectra analysis of denaturing of RSN 5 through a temperature ranging from 20° to 90° C.
Figure 30:
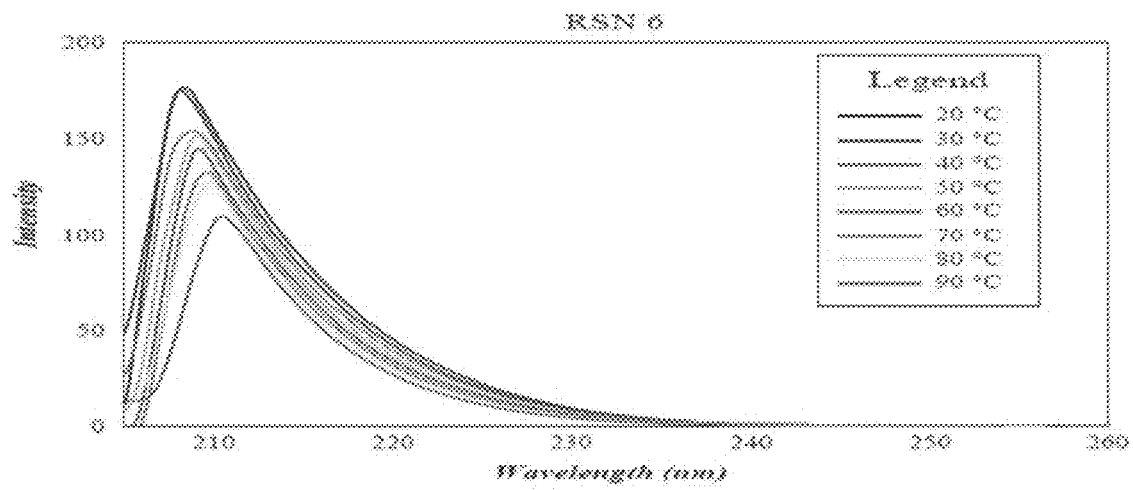
FIG. 30 shows a spectra analysis of denaturing of RSN 4 through a temperature ranging from 20° to 90° C.

RSN 1, RSN 4 and RSN 6 shown in FIG. 25, FIG. 28 and FIG. 30 reflect a random coil with a positive band between 200 and 220 nm. For RSN 1, the protein starts to denature at 50° C. and denatures further at 70° C., for RSN 4, the protein also starts to denature at 50° C. and denatures further at 90° C. For RSN 6 the protein denatures at 40° C. and slowly denatures until 90° C. RSN 2 shows a double negative band between 200-220 nm indicating an α-helix. As the temperature increases RSN 2 starts to denature at 70° C. shown in FIG. 26. RSN 5 shows a negative band round 220 nm indicating there is a β-sheet in the protein. As the temperature increases RSN 5 starts to denature at 60° C. and fully denatures at 70° C. (shown in FIG. 29). RSN 3, much like RSN 5, shows a negative band around 220 nm indicating a β-sheet in the protein. Once the temperature reaches 70° C., RSN 3 fully denatures (shown in FIG. 27) (Wavelength (nm) 210 220 230 240 250 260 Intensity).

Conclusion

RSN 2 has an α-helix indicated by the double negative band between 200-220 nm and with the addition of heat the protein will start to denature. At 70° C. the protein starts to lose the distant double band, resulting in the RSN 2 secondary structure staying intact up to 60-69° C. RSN 3 and 5 have an β-sheet indicated by a single negative band between 200-220 nm and with the addition of heat the protein will start to denature. At 70° C. the protein starts to lose the distant single band, resulting in RSN 3 and 5 secondary structure staying intact up to 60-69° C. RSN 1 and 4 has a random coil with a single positive band between 200-220 nm and with addition of heat the protein will start to denature. At 50° C. RSN 1 starts to denature and further denatures at 70° C. RSN 4, starts to denature at 50° C. and further denatures at 90° C., with the distinct positive band starting to decrease in intensity. The results show that RSN 1 and RSN 4 secondary structures stay intact up to 40-49° C. RSN 6 also has a positive band between 200-220 nm indicating a random coil and with the addition of heat, the protein starts denaturing at 40° C. and slowly denatures until 90° C. RSN 6 as a secondary structure staying intact up to 30-39° C.

Ranaspumin Protein (RSN 2) Utilized as a Stabilizer for Liposomes Encapsulating Cannabidiol (CBD)

It was found over the past few decades that the stability of liposomes in biological fluids is dramatically improved by using formulations composed of neutral long-chain saturated phospholipids and cholesterol.[21] It has also be found that the half-life of liposomes without stabilizer has been around 12-24 hours[22], with the use of a stabilizer such as polyoxyethylene glycol (PEG), the life time of a liposome increases drastically.[22-23] In order for a chemical to be used as a stabilizer/surfactant for liposomes, the chemical should have a hydrophilic polymer which attracts a water layer to the liposome surface.[21-23]

Aim of Experiment

With the use of an Atomic Force Microscopy (AMF), a liposome can be measured for size and quality of liposomes in a 1-105 μm square region. RSN 2 can be classified as surfactant by the fact that RSN 2 can lower the surface tension of a liquid. Liposome have a half-life of 12-24 hours but, with the use of a surfactant/stabilizer, the lifetime increases. RSN 2 in a 3% glycerol solution could be used to extend the lifetime of a liposome incapsulated in a drug and be monitored by AFM.

Experimental Step-Up

RSN 2 was lyophilized then diluted down from a 10% glycerol solution to a 3% glycerol solution. The following mixture had a final concentration of 1.99 mg/mL. To make the liposomes, 50 mL of ethanol was added to a 200 mL round bottom flask and heated to 40° C. 1.5 g of phosphatidylcholine was added to the flask and consistently stirred until completely dissolved. Once dissolved, 0.5 g of cholesterol along with 50 mL of the RSN 2 solution with a concentration of 1.99 mg/mL was added to the flask until completely dissolved. 0.5 g of CBD was added to the flask and stirred until dissolved.

The solution was then placed onto a rotavap for 45 minutes until all the solvent was removed. 50 mL of mili Q water was added to the flask and vigorously shook until all solid was removed from the sides of the flask and dissolved. The sample was sonicated for 15 minutes with 10 seconds on and 15 seconds off at an amplitude of 60. After the sample was sonicated, the liposomes were analyzed using an AFM.

To prepare the sample for the AFM, 999 μL of mili Q water was placed into a 1.5 mL Eppendorf tube. 1 μL of the liposome mixture was added and vortexed for 10 seconds. A Muscovite Mica V4 15 mm diameter, 0.15 mm-0.21 mm thickness was cleaved and 10 μL of samples were placed on the mica sheet. The sample was then dried using a heat gun until there was no liquid left on the mica sheet. The mica sheet was then placed onto the nano surf AFM.

The laser was aligned to at least 50% detector intensity. The cantilever was selected to ACL-A (solid samples), the instrument set to dynamic force, and a frequency sweep was conducted ensuring that the step frequency was set to 1000 Hz and the free vibration was set to 500 mV. The parameters for each run was set for image size at 5 μm, time/line at 0.98 s, points/line at 256 and rotation set to 0. The Z-controller parameters were set for points set at 65%, I-Gain was set to 2000, P-Gain and D-Gain were set to 0. The cantilever was lowered to the sample and an image is collected in about 8.0 minutes. Once the image was collected, a scan was collected of a close-up image ranging from 1-2 μm, the points/line was changed to 512 and the time/line was changed to 1.2 s. The image was then captured in roughly 20 minutes and used to measure the average radius of each liposome.

Results

Figure 31A:
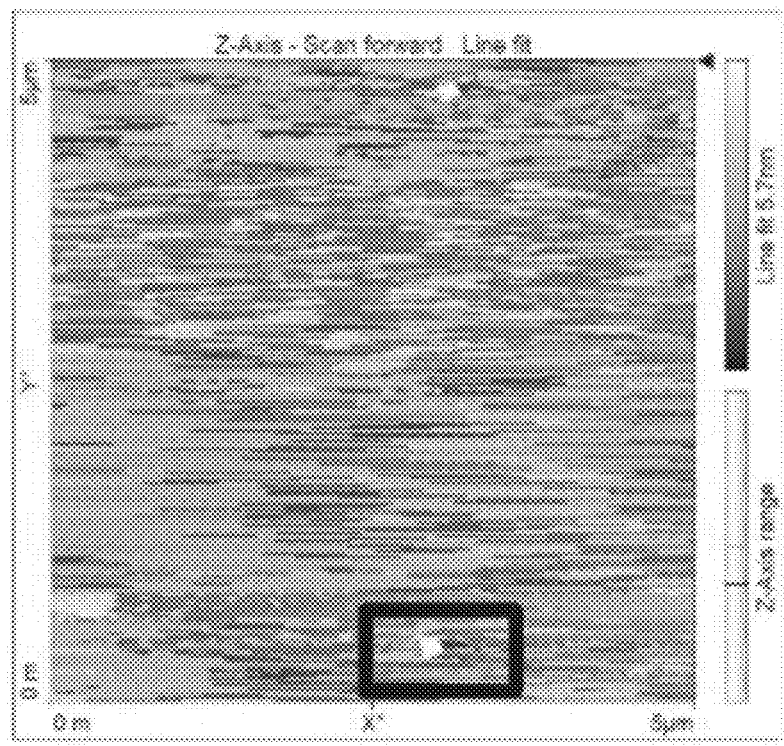
FIG. 31a shows an image of liposomes without stabilizer after 24 hours. The black square is the location of the zoomed in image in FIG. 31b.
Figure 31B:
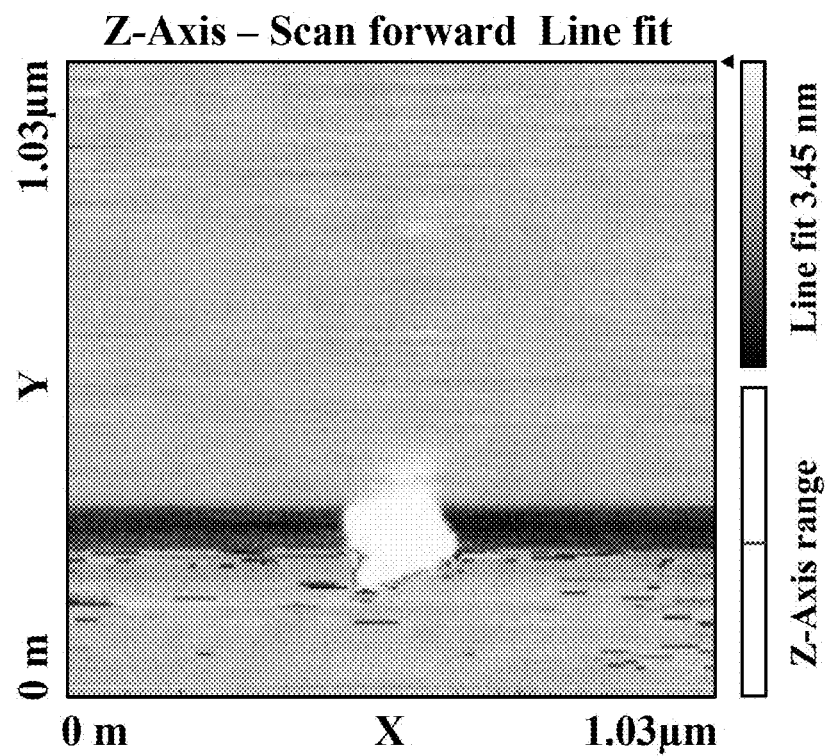
FIG. 31b shows a zoomed in image of liposomes without stabilizer after 24 hours.
Figure 32A:
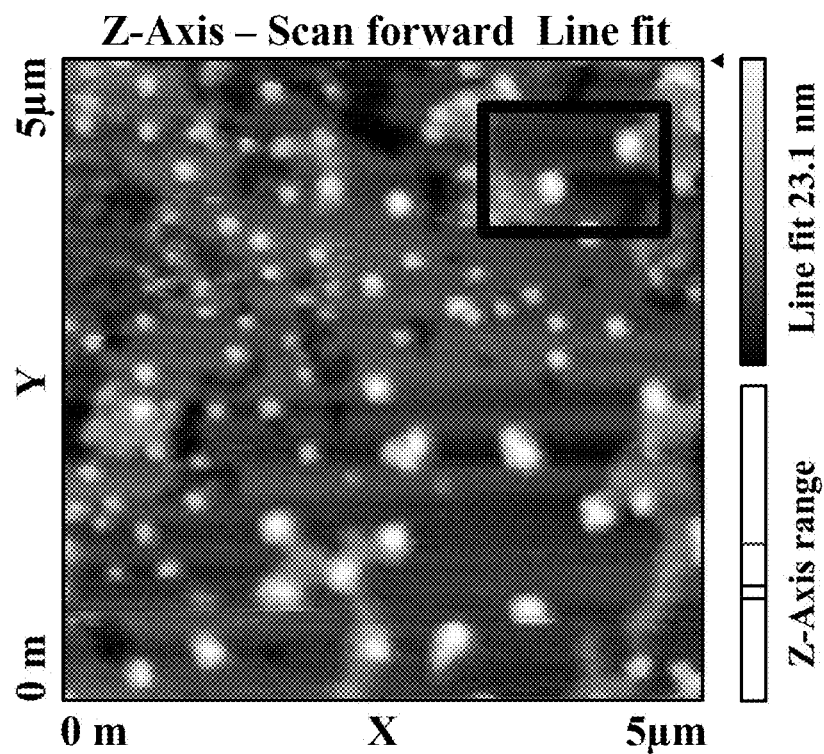
FIG. 32a shows an image of liposomes with stabilizer after 24 hours. The black square is the location of the zoomed in image in FIG. 32b.
Figure 32B:
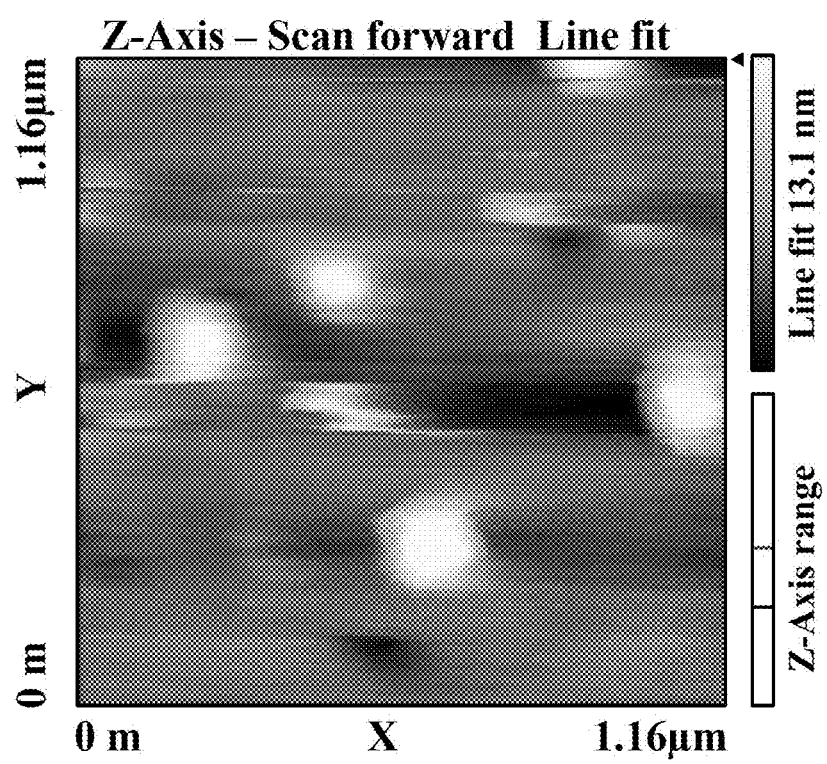
FIG. 32b shows a zoomed in image of liposomes with stabilizer after 24 hours.
Figure 33A:
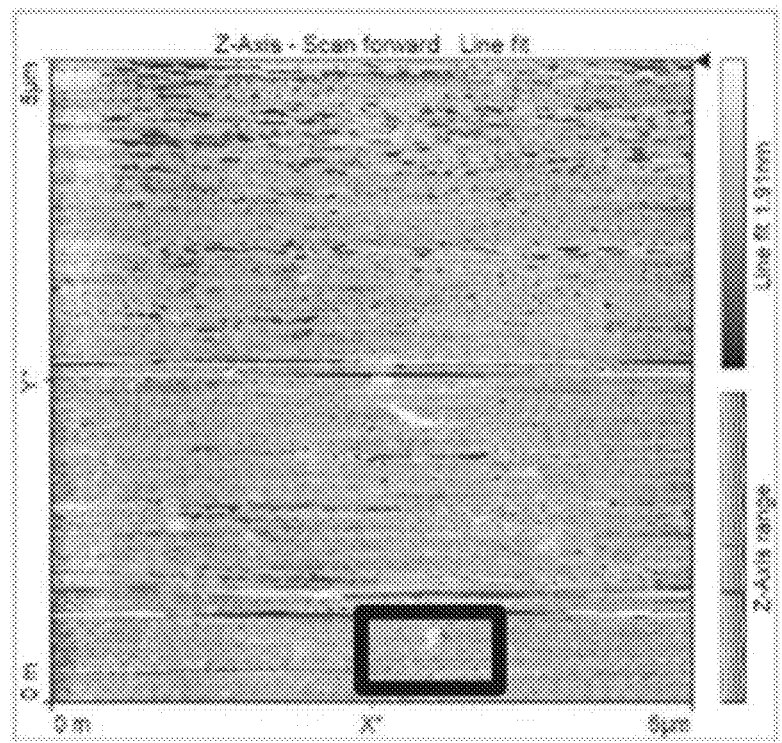
FIG. 33a shows an AFM image of liposomes without stabilizer after 96 hours. The black square is the location of the zoomed in image in FIG. 33b.
Figure 33B:
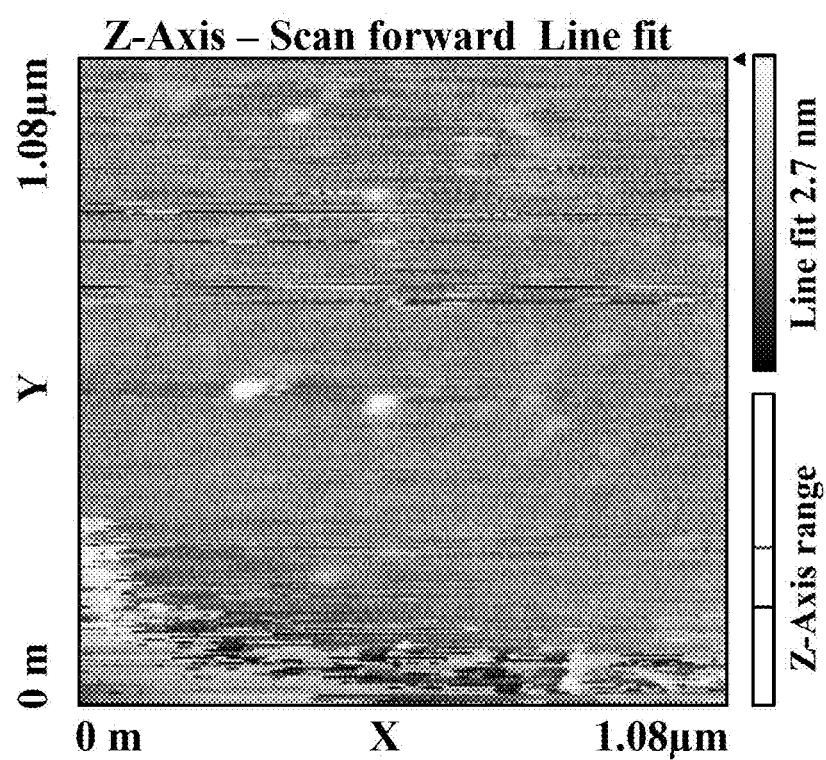
FIG. 33b shows a zoomed in AFM image of liposomes without stabilizer after 96 hours.
Figure 34A:
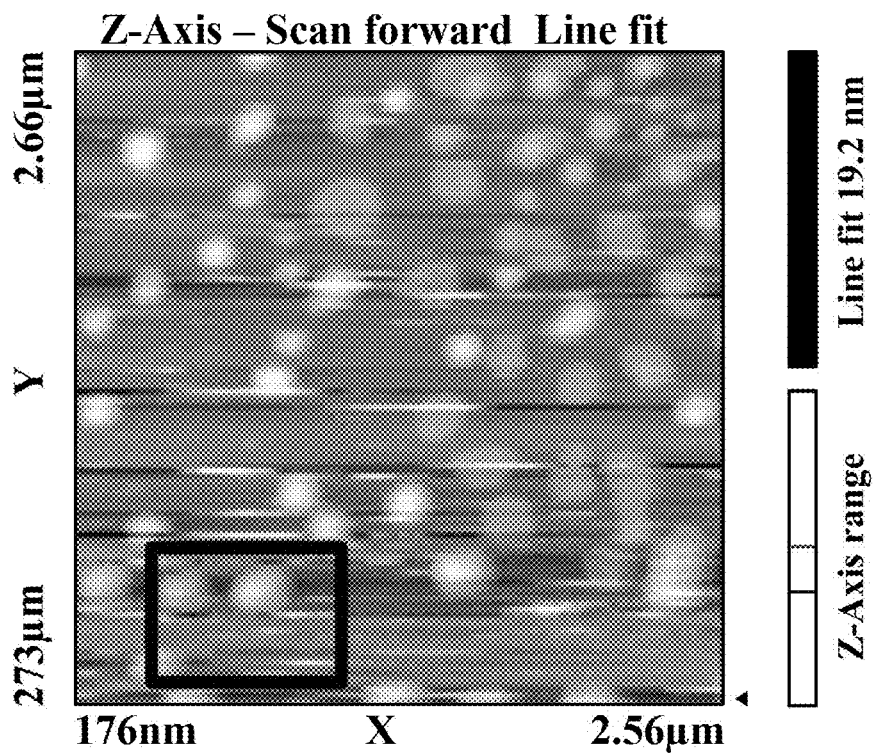
FIG. 34a shows an AFM image of liposomes with stabilizer after 96 hours. The black square is the location of the zoomed in image in FIG. 34b.
Figure 34B:
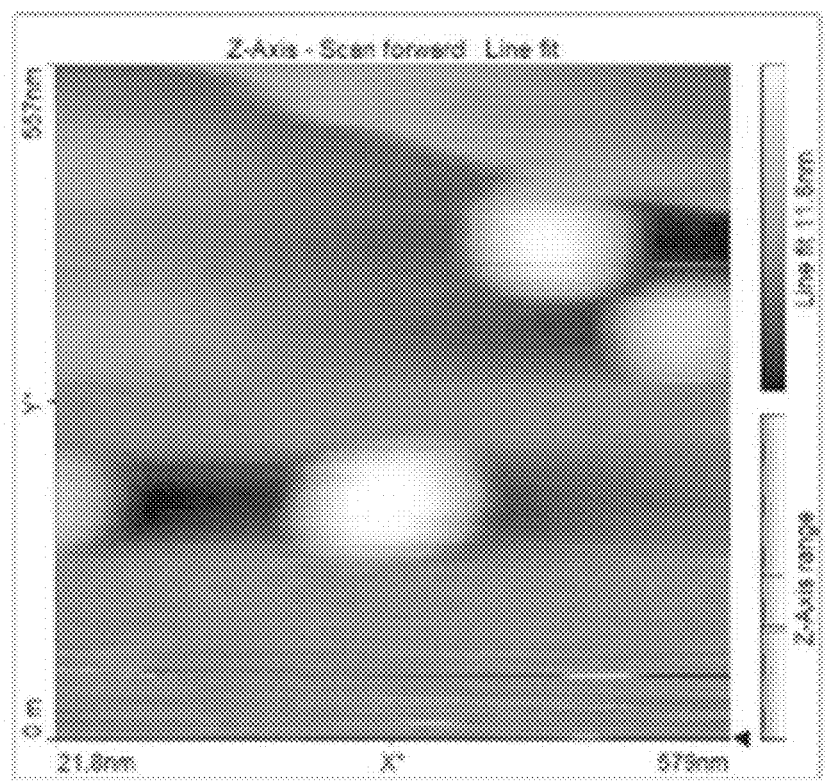
FIG. 34b shows a zoomed in AFM image of liposomes with stabilizer after 96 hours.

An AFM image was taken of the liposomes to confirm the formation and capsulation of CBD after 24 hours. FIG. 31a shows the liposomes without stabilizer. FIG. 31b shows a zoomed in image of the liposomes from 5 μm to 1 μm. FIG. 32a shows the liposomes with the foam stabilizer after 24 hours and FIG. 32b shows a zoomed in image of the liposomes with the foam as a stabilizer from 5 μm to 1 μm. The liposomes without stabilizer had an average radius of 47.2 nm and the liposomes with the foam as a stabilizer had an average radius of 43.3 nm. To calculate the radius of the liposomes equation 1 was used.

$$r = \sqrt{\frac{l*[(2*h)+l]}{4}} \quad \text{eq. (1)}$$

Where r is the radius of the liposome, l is the length of the liposome obtained from the software nanosurf, h is the height of the liposome also obtained from the software nanosurf. Another AFM image was obtained after 96 hours; the image obtained from the sample without a stabilizer is shown in FIGS. 33a and 33b with an average radius of 31.6 nm. The sample with the foam as a stabilizer is shown in FIGS. 34a and 34b with an average radius of 43.3 nm.

Figure 35:
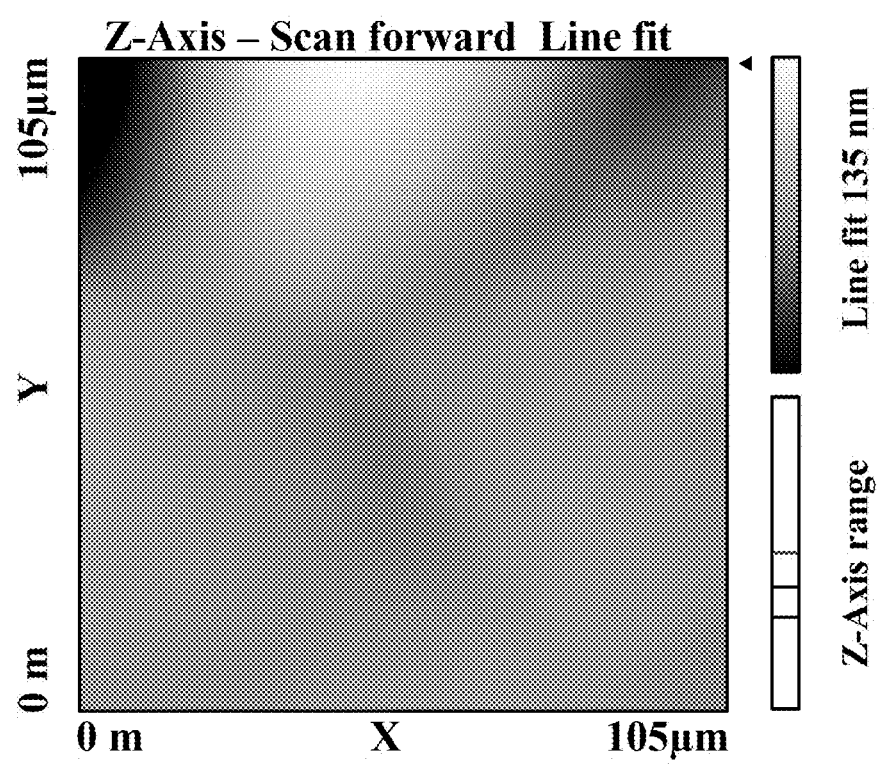
FIG. 35 shows an AFM image of liposomes with stabilizer after 96 hours.
Figure 36A:
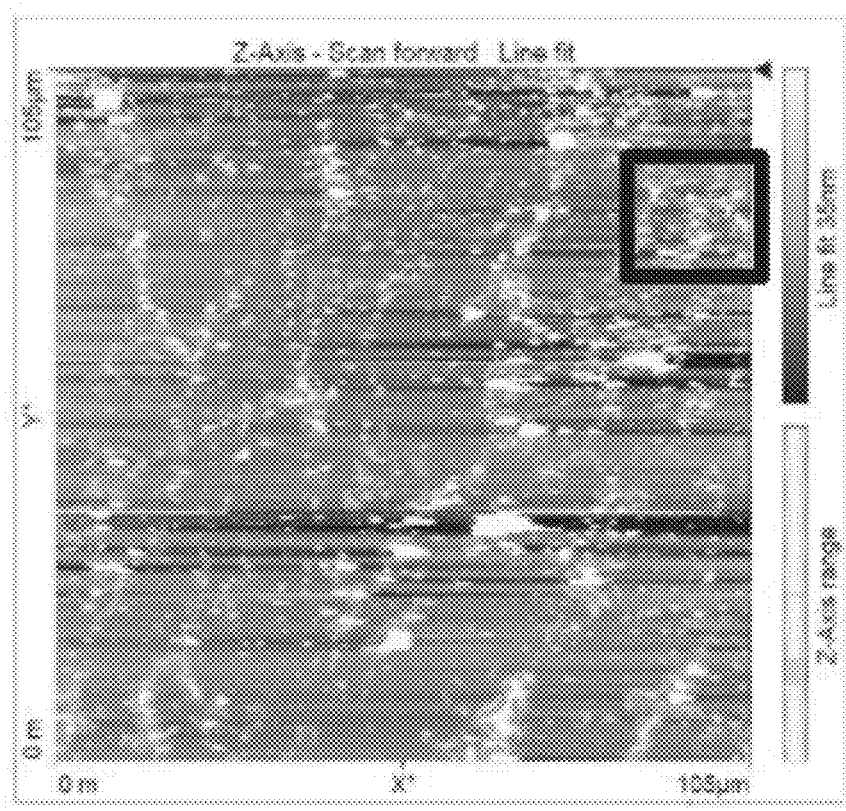
FIG. 36a shows an AFM image of liposomes with stabilizer after 1 month. The black square is the location of the zoomed in image in FIG. 36b.
Figure 36B:
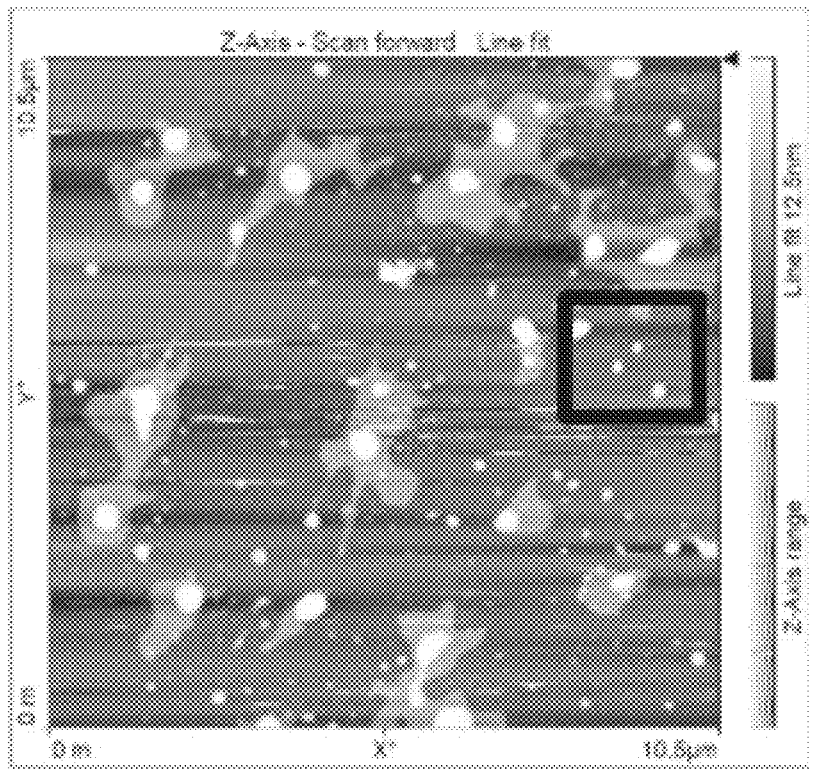
FIG. 36b shows a zoomed in AFM image of liposomes with stabilizer after 1 month. The black square is the location of the zoomed in image in FIG. 36c.
Figure 36C:
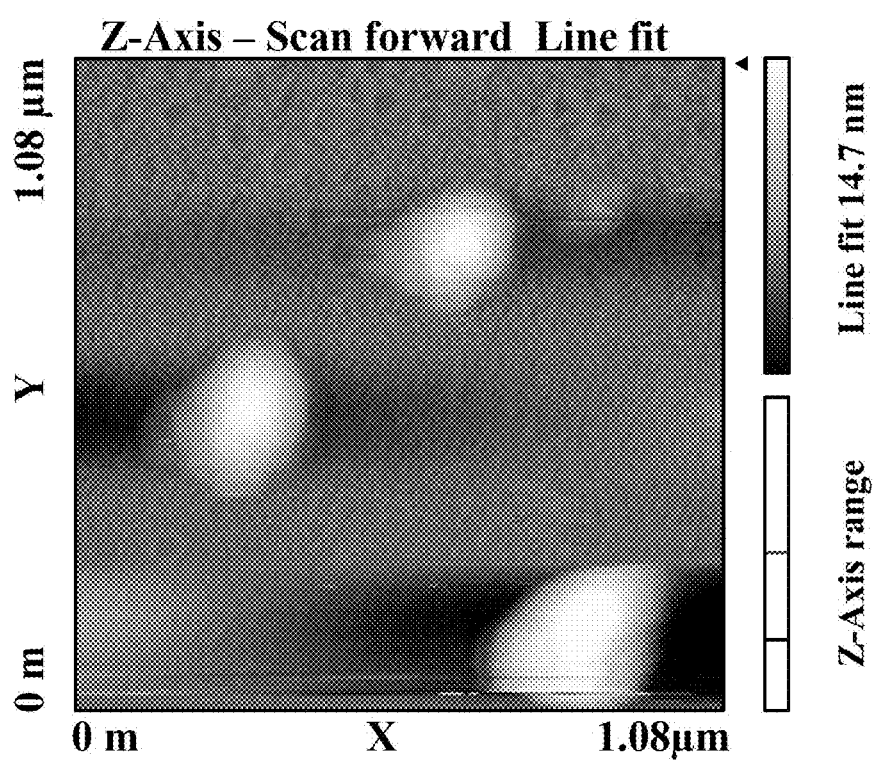
FIG. 36c shows a zoomed in AFM image of liposomes with stabilizer after 1 month.
Figure 37:
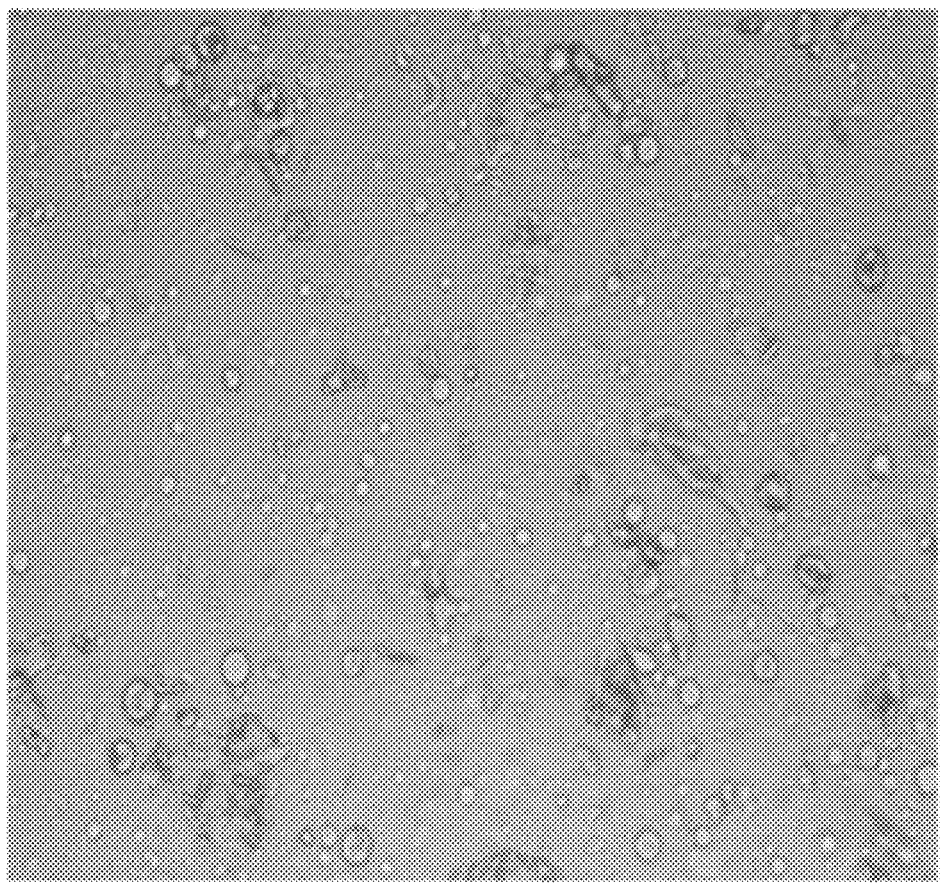
FIG. 37 shows a microscope image of liposomes with stabilizer after two months.

After 1 month, an AFM image was taken of both the foam stabilized liposomes and the liposomes without a stabilizer. For the 1-month samples, a full scan was taken from 0 to 105 m, then zoomed in to obtain a full visual of the sample after 1 month. FIG. 35 shows the liposome sample without stabilizer, FIG. 36a, FIG. 36b and FIG. 36c shows the liposome sample with the foam as a stabilizer with an average radius of 63.43 nm. FIG. 37 reflects a microscope image of the liposomes with foam as a stabilizer after 2 months. After 2 months the liposomes had an average radius of 108.3 nm.

Conclusion

After 24 hours the liposome sample without stabilizer was challenging to obtain. An image at the 24 hour mark and after 96 hours the liposomes started to degrade and aggregate together. At the 1 month mark a full scan from 0 to 105 μm was taken of the liposomes showing that the liposomes had aggregated together so an average radius could not be obtained from the 1 month mark. While the liposomes with RSN 2 as a stabilizer after 24 hours where easier to obtain an image, and retained a spherical shape after 24 hours, at the 96 hour mark the liposome had some aggregation but, still retained their shape and size. After 1 month, the liposomes with RSN 2 as a stabilizer did in fact aggregate together with an average radius of 63.43 nm from 43.3 nm but, while looking at the full scan 0-105 μm, the sample still had liposomes widely spread through the solution. After 2 months, the liposomes still retained their shape but increased in size to 103.8 nm. Further scans can be conducted to see how long the liposomes can contain their size and shape.

Standard Operating Procedure for Recombinant Protein Production Using *E. coli*

1. The recombinant bacterial stock culture obtained from the manufacturer (VectorBuilder.com) were stored in a 50:50 glycerol:water stock solution and were placed in a −80° C. freezer.

2. Upon removal from the freezer the bacterial strains were inoculated and placed on LB ampicillin agar plates to allow the *E. coli* to grow into individual colonies at 37° C. overnight.

3. Once the colonies were large enough, the colonies were extracted and grown into small LB ampicillin 100 mL cultures. These cultures were then grown for 2 days at 37° C. with shaking until the optical density was 0.6.

4. Next, 1 L of LB ampicillin media was inoculated with 20 mL of solution from the small culture and placed in an incubator shaker at 37° C. for 6 hours.

5. Once the bacterial cells were grown, the ranaspumin proteins were expressed by placing IPTG into the culture to a final concentration of 1 mM and left overnight at room temperature with shaking.

6. Once expression of the proteins was complete, the large culture was removed, and purification of protein was started.

Protein Purification

1. Purification of each protein was completed by first removing the 1 L bacterial culture and separating into 20×50 mL centrifugal tubes. These tubes were then centrifuged for 20 minutes at 10,000 rpm.

2. The supernatant was removed and discarded. The remaining pellets of the 20 tubes were then combined into 5 tubes to be frozen at −80° C. for 2 days.

3. After 2 days, the samples were removed and 40 mL of NPI-10 buffer was added to each of the tubes. The tubes were then subjected to sonication using a cell dismembrator. The tubes were placed in an ice bath and sonicated in intervals of 30 seconds on and 1 minute off at 80% amplitude.

4. After sonication, the samples were placed in then placed in the centrifuge at 4° C. and run at 12,000 rpm for 20 minutes. This run was conducted a second time to ensure no cell fragments remained in the supernatant. The supernatant was then removed and stored at 4° C. overnight.

5. The samples were then subjected to nickel affinity column purification to extract only the proteins of interest using a Novagen His-Bind Resin Purification Kit. This kit allows up to 10 mg of each protein to be extracted during each run.

6. The process first starts by placing 2 mL of resin into the column and letting the resin settle using gravity filtration. Next, 5 mL of charge buffer is placed in the column. This provides the nickel substrate of the column, which the protein will bind to due to the histidine tag. Once the charge buffer is completed, 3 mL of binding buffer is used to clean the column of any contaminants.

7. The sample extract (200 mL) is then placed on the column. To ensure proper extraction, a flow of 10 mL per hour was used. Once the sample extract was completed, another wash was completed to remove all contaminants in the column.

8. Finally, an elute buffer was used to extract the protein from the column into 6 mL of buffer. This buffer was then removed and upon agitation a foam was formed.

9. A secondary purification to make the solution increase in concentration from 1 mg/mL to 10 mg/mL was achieved using a Sartorius Vivaspin 20 centrifugal tube. This tube had a 10,000 molecular weight cut off (MWCO), allowing only proteins larger than 10,000 molecular weight to remain in the solution. About 1-1.5 ml of protein is obtained from a 1 L starter culture.

10. This solution was then extracted and lyophilized overnight to remove all remaining contaminants and solvents from the proteins. The proteins were then analyzed using ESI-MS for confirmation of protein synthesis.

Summary of Embodiments of the Present Disclosure

According to Clause 1, a synthetic Túngara frog foam is provided. The synthetic Túngara frog foam includes synthetically synthesized ranaspumin proteins (RSN), wherein only active segments of the RSN proteins are synthesized and signal peptides, if present, are effectively removed, and a sugar backbone, wherein synthesis of only the active segments of the RSN proteins results in proper folding of the protein and allows surfactant capabilities to be retained in the synthetic foam, wherein the synthetic foam maintains stability for greater than 10 days without any dehydration or loss of foam structure due to surface tension effects.

According to Clause 2, the synthetic Túngara frog foam of Clause 1 has a stability that is up to 5 times greater than natural Túngara frog foam.

According to Clause 3, the synthetic Túngara frog foam of Clause 1 or Clause 2 includes ranaspumin proteins (RSN) having six synthetically synthesized ranaspumin proteins, wherein the ranaspumin (RSN) proteins include—ranaspumin-1 (RSN-1) of synthetic amino acid sequence no. 1; ranaspumin-2 (RSN-2) of synthetic amino acid sequence no. 2; ranaspumin-3 (RSN-3) of synthetic amino acid sequence no. 3; ranaspumin-4 (RSN-4) of synthetic amino acid sequence no. 4; ranaspumin-5 (RSN-5) of synthetic amino acid sequence no. 5; and, ranaspumin-6 (RSN-6) of synthetic amino acid sequence no. 6.

According to Clause 4, the synthetic Túngara frog foam of any of Clauses 1-3, wherein the sugar backbone includes six synthetically synthesized polysaccharides, wherein the polysaccharides include 4 tetrasaccharides, a heptasaccharide and a nonasasscharide, further wherein the polysaccharides all include at least one free hydroxyl group to bind to RSN proteins via a serine or threonine amino acid.

According to Clause 5, the synthetic Túngara frog foam of any of Clauses 1-4, wherein the ranaspumin proteins all comprise one or more serine or threonine for binding via an F-type fucolectin.

According to Clause 6, the synthetic Túngara frog foam of any of Clauses 1-5, wherein the ranaspumin proteins are fucolectin type proteins including one or more of serine or threonine which bind to the hydroxyl group at the 1 position of one of the polysaccharides.

According to Clause 7, the synthetic Túngara frog foam of any of Clauses 1-6, wherein the polysaccharides all comprise at least one free hydroxyl group which binds to the ranaspumin proteins via a serine or a threonine amino acid.

According to Clause 8, the synthetic Túngara frog foam of any of Clauses 1-7, wherein ranaspumin protein 2 (RSN-2) is used as a stabilizer for liposomes encapsulating cannabidiol (CBD).

According to Clause 9, the synthetic Túngara frog foam of any of Clauses 1-8, wherein the molecular weights of the RSN proteins with no histidine tags attached are as follows: 11.38 kDa for RSN-1, 11.11 kDa for RSN-2, 18.85 kDa for RSN-3, 19.26 kDa for RSN-4, 18.73 kDa for RSN-5, and 25.69 kDa for RSN-6.

According to Clause 10, the synthetic Túngara frog foam of any of Clauses 1-9, wherein the frog foam is 85 angstroms thick.

According to Clause 11, the synthetic Túngara frog foam of any of Clauses 1-10, wherein the RSN protein is expressed by E. coli vectors containing a LacO gene promoter upstream of a subcloned RSN gene upon induction with isopropyl β-D-1-thiogalactopyranoside, wherein the subcloned RSN gene contains an ampicillin resistant gene.

According to Clause 12, the synthetic Túngara frog foam of any of Clauses 1-11, wherein the RSN protein comprises a histidine tag for extraction by nickel affinity column purification.

According to Clause 13, provided is a pulmonary drug delivery composition including the synthetic Túngara frog foam of any of Clauses 1-12 as a surfactant.

According to Clause 14, provided is a fracking foam including the synthetic Túngara frog foam composition of any of Clauses 1-12 as a surfactant wherein the RSN proteins extract aromatic compounds and carbon chain aliphatics.

According to Clause 15, provided is a pesticide/insecticide including the synthetic Túngara frog foam composition of any of Clauses 1-12 as a surfactant.

According to Clause 16, the pesticide of Clause 15 further including bifenazate.

According to Clause 17, the pesticide of Clause 15 or Clause 16, wherein the concentration of pesticide on a leaf including synthetic Túngara frog foam as a component of the pesticide is 3.6 times the amount of pesticide on a leaf which does not include synthetic Túngara frog foam 5 days after treatment and wherein the concentration of pesticide on a leaf including synthetic Túngara frog foam as a component of the pesticide is 1.2 times the amount of pesticide on a leaf which does not include synthetic Túngara frog foam 10 days after treatment.

According to Clause 18, provided is an antibacterial including the synthetic Túngara frog foam composition of any of Clauses 1-12 as a surfactant.

According to Clause 19, the antibacterial of Clause 18 is provided wherein RSN-2 kills bacteria such as E. coli and RSN-5 slows the rate of growth of bacteria such as E. coli.

According to Clause 20, the antibacterial of Clause 18 or Clause 19, wherein the antibacterial is used to protect and maintain living tissue for transportation.

According to Clause 21, provided is an antimicrobial including the synthetic Túngara frog foam composition of any of Clauses 1 and 3-12, wherein the synthetic ranaspumin proteins are ranaspumin-2 (RSN-2) including synthetic amino acid sequence no. 2 and ranaspumin-5 (RSN-5) including synthetic amino acid sequence no. 5.

According to Clause 22, provided is a foam composition for food storage and transport including the synthetic Túngara frog foam composition of any of Clauses 1-12 as a surfactant, a gas, and an aqueous carrier.

According to Clause 23, the foam composition of Clause 22, wherein the composition is applied to live crustaceans for transport.

According to Clause 24, provided is a method for storing and transporting fresh food, the method including the following steps: a) placing fresh food in a receptacle suitable for storing and transporting fresh food; b) providing a synthetic foam composition according to any one of Clauses 1-12 including a food grade synthetic surfactant selected from the list of ranaspumin-1, ranaspumin-2, ranaspumin-3, ranaspumin-4, ranaspumin-5, or ranaspumin-6; and c) at least partially covering the fresh food with the foam composition.

According to Clause 1, a synthetic Túngara frog foam is provided including synthetically synthesized ranaspumin proteins (RSN), wherein only active segments of the RSN proteins are synthesized and signal peptides, if present, are effectively removed, and a sugar backbone, wherein synthesis of only the active segments of the RSN proteins results in proper folding of the protein and allows surfactant capabilities to be retained in the synthetic foam, wherein the synthetic foam maintains stability for greater than 10 days without any dehydration or loss of foam structure due to surface tension effects.

According to Clause 2, the synthetic Túngara frog foam composition of Clause 1, wherein the ranaspumin proteins (RSN) include six synthetically synthesized ranaspumin proteins, wherein the ranaspumin (RSN) proteins include— ranaspumin-1 (RSN-1) including synthetic amino acid sequence no. 1; ranaspumin-2 (RSN-2) including synthetic amino acid sequence no. 2; ranaspumin-3 (RSN-3) including synthetic amino acid sequence no. 3; ranaspumin-4 (RSN-4) including synthetic amino acid sequence no. 4; ranaspumin-5 (RSN-5) including synthetic amino acid sequence no. 5; and, ranaspumin-6 (RSN-6) including synthetic amino acid sequence no. 6.

According to Clause 3, the synthetic Túngara frog foam composition of Clause 1 or Clause 2, wherein the sugar backbone includes six synthetically synthesized polysaccharides wherein the polysaccharides include 4 tetrasaccharides, a heptasaccharide and a nonasasscharide, further wherein the polysaccharides all include at least one free hydroxyl group to bind to RSN proteins via a serine or threonine amino acid.

According to Clause 4, the synthetic Túngara frog foam composition of any of Clauses 1-3, wherein the ranaspumin proteins are fucolectin type proteins including one or more of serine or threonine which bind to the hydroxyl group at the 1 position of one of the polysaccharides.

According to Clause 5, the synthetic Túngara frog foam composition of any of Clauses 1-4, wherein the polysaccharides all include at least one free hydroxyl group which binds to the ranaspumin proteins via a serine or a threonine amino acid.

According to Clause 6, the synthetic Túngara frog foam composition of any of Clauses 1-5, wherein ranaspumin protein 2 (RSN-2) is used as a stabilizer for liposomes encapsulating cannabidiol (CBD).

According to Clause 7, the synthetic Túngara frog foam composition of any of Clauses 1-6, wherein the molecular weights of the RSN proteins with no histidine tags attached are as follows: 11.38 kDa for RSN-1, 11.11 kDa for RSN-2, 18.85 kDa for RSN-3, 19.26 kDa for RSN-4, 18.73 kDa for RSN-5, and 25.69 kDa for RSN-6.

According to Clause 8, the synthetic Túngara frog foam composition of any of Clauses 1-7, wherein the frog foam is 85 angstroms thick.

According to Clause 9, the synthetic Túngara frog foam composition of any of Clauses 1-8, wherein the RSN protein is expressed by $E.$ $coli$ vectors containing a LacO gene promoter upstream of a subcloned RSN gene upon induction with isopropyl $\beta$-D-1-thiogalactopyranoside, wherein the subcloned RSN gene contains an ampicillin resistant gene.

According to Clause 10, the synthetic Túngara frog foam composition of any of Clauses 1-9, wherein the RSN protein comprises a histidine tag for extraction by nickel affinity column purification.

According to Clause 11, provided is a pulmonary drug delivery composition including the synthetic Túngara frog foam composition of any of Clauses 1-10 as a surfactant.

According to Clause 12, provided is a fracking foam including the synthetic Túngara frog foam composition of any Clauses 1-10 as a surfactant wherein the RSN proteins extract aromatic compounds and carbon chain aliphatics.

According to Clause 13, provided is a pesticide/insecticide including the synthetic Túngara frog foam composition of any of Clauses 1-10 as a surfactant.

According to Clause 14, provided is the pesticide of Clause 13 including bifenazate.

According to Clause 15, provided is the pesticide of Clause 14, wherein the concentration of pesticide on a leaf including synthetic Túngara frog foam as a component of the pesticide is 3.6 times the amount of pesticide on a leaf which does not include synthetic Túngara frog foam 5 days after treatment and wherein the concentration of pesticide on a leaf including synthetic Túngara frog foam as a component of the pesticide is 1.2 times the amount of pesticide on a leaf which does not include synthetic Túngara frog foam 10 days after treatment.

According to Clause 16, provided is an antibacterial including the synthetic Túngara frog foam composition of any of Clauses 1-10 as a surfactant.

According to Clause 17, the antibacterial of Clause 16, wherein the antibacterial is used to protect and maintain living tissue for transportation.

According to Clause 18, provided is an antimicrobial including the synthetic Túngara frog foam composition of any of Clauses 1-10, wherein the synthetic ranaspumin proteins are ranaspumin-2 (RSN-2) including synthetic amino acid sequence no. 2 and ranaspumin-5 (RSN-5) including synthetic amino acid sequence no. 5.

According to Clause 19, provided is a foam composition for food storage and transport including the synthetic Túngara frog foam composition of any of Clauses 1-10 as a surfactant, a gas, and an aqueous carrier.

According to Clause 20, the foam composition of Clause 19, wherein the composition is applied to live crustaceans for transport.

According to Clause 21, provided is a method for storing and transporting fresh food, the method comprising: a) placing fresh food in a receptacle suitable for storing and transporting fresh food; b) providing a synthetic foam composition according to any of Clauses 2-10 including a food grade synthetic surfactant selected from the list of ranaspumin-1, ranaspumin-2, ranaspumin-3, ranaspumin-4, ranaspumin-5, or ranaspumin-6; and c) at least partially covering the fresh food with the foam composition.

While embodiments of the disclosure have been illustrated and described as noted above, many changes can be made without departing from the spirit and scope of the disclosure. For example, by substituting similar size, charge and function amino acids. Variations on the sequences and polysaccharides disclosed are possible, found to fold accordingly and exhibit surfactant characteristics and longevity due to the sugars and seek protections of a variety of amino acid compositions. Accordingly, the scope of the disclosure is not limited by the disclosure of the preferred embodiment. Instead, the present disclosure should be determined entirely by reference to the claims that follow.

REFERENCES

1. Fleming, R. I.; Mackenzie, C. D.; Cooper, A.; Kennedy, M. W., Foam nest components of the Túngara frog: a cocktail of proteins conferring physical and biological resilience. *Proceedings of the Royal Society of London B: Biological Sciences* 2009, rspb. 2008.1939.
2. Shepard, D. B.; Caldwell, J. P., From foam to free-living: ecology of larval *Leptodactylus labyrinthicus*. *Copeia* 2005, 2005(4), 803-811.
3. Ferraro, D. P.; Pereyra, M. E.; Baldo, J. D.; Faivovich, J., The clutch structure of *Pleurodema tucumanum* (Anura: Leptodactylidae). 2016.
4. Dalgetty, L.; Kennedy, M. W., Building a home from foam-túngara frog foam nest architecture and three-phase construction process. *Biology letters* 2010, 6 (3), 293-296.
5. Hill, C.; Eastoe, J., Foams: From nature to industry. *Advances in colloid and interface science* 2017, 247, 496-513.
6. Hissa, D. C.; Bezerra, W. M.; Freitas, C. D. T. D.; Ramos, M. V.; Lopes, J. L. D. S.; Beltramini, L. M.; Roberto, I. J.; Cascon, P.; Melo, V. M. M., Frog foam nest protein diversity and synthesis. *Journal of Experimental Zoology Part A: Ecological Genetics and Physiology* 2016, 325 (7), 425-433.
7. Brandani, G. B.; Vance, S. J.; Schor, M.; Cooper, A.; Kennedy, M. W.; Smith, B. O.; MacPhee, C. E.; Cheung, D. L., Adsorption of the natural protein surfactant Rsn-2 onto liquid interfaces. *Physical Chemistry Chemical Physics* 2017, 19 (12), 8584-8594.
8. Cooper, A.; Vance, S. J.; Smith, B. O.; Kennedy, M. W., Frog foams and natural protein surfactants. *Colloids and Surfaces A: Physicochemical and Engineering Aspects* 2017, 534, 120-129.
9. Drickamer, K., F-Type Lectins. *Biotechnology and Biological Sciences Research Council* 2014, 1, 1.
10. Garrozzo, D.; Impallomeni, G.; Spina, E.; Sturiale, L.; Zanetti, F., Matrix□assisted laser desorption/ionization mass spectrometry of polysaccharides. *Rapid communications in mass spectrometry* 1995, 9 (10), 937-941.
11. Venkataraman, G.; Shriver, Z.; Raman, R.; Sasisekharan, R., Sequencing complex polysaccharides. *Science* 1999, 286 (5439), 537-542.
12. Dong, H. Efficient carbohydrate synthesis by controlled inversion strategies. KTH, 2006.
13. Pistorio, S., Development of an HPLC-based oligosaccharide synthesizer. 2017.
14. Hjuler, C. T.; Maolanon, N. N.; Sauer, J.; Stougaard, J.; Thygesen, M. B.; Jensen, K. J., Preparation of glycoconjugates from unprotected carbohydrates for protein-binding studies. *nature protocols* 2017, 12 (11), 2411.
15) Cooper A, Kennedy MW. 2010. Biofoams and natural protein surfactants. Biophys. Chem. 151:96-104
16) Bognolo, G. Biosurfactants as emulsifying agents for hydrocarbons. Colloids and Surfaces A: Colloids Surf., A. 1999, 152, 41-52.
17) Holder, A. I. The Wet Disc Antimicrobial solution assay an in Vitro Method to Test Efficacy of antimicrobial Solutions for Tropical Use. J. Burn Care Rehabil. 1989, 10, 203-208.
18) Squire, M. W.; Ludwig, B. J.; Thompson, J. R.; Jagodzinski, J.; Hall, D.; Andes, D. Premixed antibiotic bone cement: an in vitro comparison of antimicrobial efficacy. The Journal of arthroplasty 2008, 23, 110-114.
19) Hennessey, J. P.; Johnson, C. W. Information content in the circular dichroism of proteins. Biochemistry 1981, 20, 1085-1094
20) Holzwarth, G.; Doty, P. The Ultraviolet Circular Dichroism of Polypeptides. Am. Chem. J. 1965, 87, 218-288
21) Lasic, D. D.; Martin, F. J.; Gabizon, A.; Huang, S. K.; Papahadjopoulos, D. Sterically stabilized liposomes: a hypothesis on the molecular origin of the extended circulation times. Biochim. Biophys. Acta, Biomembr. 1991, 1070, 187-192.
22) Needham, D.; McIntosh, T. J.; Lasic, D. D. Repulsive interactions and mechanical stability of polymer-grafted lipid membranes. Biochim. Biophys. Acta, Biomembr. 1992, 1108, 40-48.
23) D. PAPAHADJOPOULOS; T M ALLEN; A GABIZON; E MAYHEW; K MATTHAYII; S K HUANG; K.-D. LEE; M C WOODLE; D LASIC; C REDEMANN; F J MARTIN Sterically stabilized liposomes: Improvements in pharmacokinetics and antitumor therapeutic efficacy., 88
24) Ahmadi Ashtiani, H. R; Bishe, P.; Lashgari, N.; Nilforoushzadeh, M. A.; Zare, S. Liposomes in Cosmetics. Journal of Skin and Stem Cell 2016, 3.

What is claimed is:

1. A synthetic Tungara frog foam comprising:
Synthetically synthesized ranaspumin proteins (RSN), wherein only active segments of the RSN proteins are synthesized and signal peptides, are effectively removed, wherein the ranaspumin proteins (RSN) comprise six synthetically synthesized ranaspumin proteins, comprising:
ranaspumin-1 (RSN-1) comprising synthetic amino acid sequence no. 1;
ranaspumin-2 (RSN-2) comprising synthetic amino acid sequence no. 2;
ranaspumin-3 (RSN-3) comprising synthetic amino acid sequence no. 3;
ranaspumin-4 (RSN-4) comprising synthetic amino acid sequence no. 4;
ranaspumin-5 (RSN-5) comprising synthetic amino acid sequence no. 5; and,
ranaspumin-6 (RSN-6) comprising synthetic amino acid sequence no. 6 and
where the synthetic Tungara frog foam further comprises a sugar backbone,
wherein synthesis of only the active segments of the RSN proteins results in proper folding of the protein and allows surfactant capabilities to be retained in the synthetic foam, wherein the synthetic foam maintains stability for greater than 10 days without any dehydration or loss of foam structure due to surface tension effects.

2. The synthetic Tungara frog foam composition of claim 1, wherein the sugar backbone comprises six synthetically synthesized polysaccharides wherein the polysaccharides comprise 4 tetrasaccharides, a heptasaccharide and a nonasasscharide, further wherein the polysaccharides all comprise at least one free hydroxyl group to bind to RSN proteins via a serine or threonine amino acid.

3. The synthetic Túngara frog foam composition of claim 2, wherein the ranaspumin proteins are fucolectin type proteins comprising one or more of serine or threonine which bind to the hydroxyl group at the 1 position of one of the polysaccharides.

4. The synthetic Túngara frog foam composition of claim 3, wherein the polysaccharides all comprise at least one free hydroxyl group which binds to the ranaspumin proteins via a serine or a threonine amino acid.

5. The synthetic Túngara frog foam composition of claim 4, wherein ranaspumin protein 2 (RSN-2) is used as a stabilizer for liposomes encapsulating cannabidiol (CBD).

6. The synthetic Túngara frog foam composition of claim 2, wherein the molecular weights of the RSN proteins with no histidine tags attached are as follows:
 11.38 kDa for RSN-1,
 11.11 kDa for RSN-2,
 18.85 kDa for RSN-3,
 19.26 kDa for RSN-4,
 18.73 kDa for RSN-5, and
 25.69 kDa for RSN-6.

7. The synthetic Túngara frog foam composition of claim 6, wherein the frog foam is 85 angstroms thick.

8. The synthetic Túngara frog foam composition of claim 1, wherein the RSN protein is expressed by *E. coli* vectors containing a LacO gene promoter upstream of a subcloned RSN gene upon induction with isopropyl β-D-1-thiogalactopyranoside, wherein the subcloned RSN gene contains an ampicillin resistant gene.

9. The synthetic Túngara frog foam composition of claim 1, wherein the RSN protein comprises a histidine tag for extraction by nickel affinity column purification.

* * * * *